US012758347B2

(12) United States Patent
Lesko et al.

(10) Patent No.: US 12,758,347 B2
(45) **Date of Patent: *Oct. 13, 2026**

(54) ULTRASONIC SURGICAL INSTRUMENT WITH INTEGRAL SHAFT ASSEMBLY TORQUE WRENCH

(71) Applicant: Cilag GmbH International, Zug (CH)

(72) Inventors: Jason R. Lesko, Cincinnati, OH (US); Matthew C. Miller, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 976 days.

This patent is subject to a terminal disclaimer.

(21) Appl. No.: 18/070,532

(22) Filed: Nov. 29, 2022

(65) Prior Publication Data

US 2023/0144673 A1 May 11, 2023

Related U.S. Application Data

(63) Continuation of application No. 16/696,329, filed on Nov. 26, 2019, now Pat. No. 11,589,942, which is a (Continued)

(51) Int. Cl.
*A61B 18/18* (2006.01)
*A61B 17/32* (2006.01)
(Continued)

(52) U.S. Cl.
CPC ...... *A61B 90/03* (2016.02); *A61B 17/320068* (2013.01); *A61N 7/02* (2013.01); (Continued)

(58) Field of Classification Search
CPC .... A61B 17/320068; A61B 2017/0046; A61B 2017/00477; A61B 2017/320069; (Continued)

(56) References Cited

U.S. PATENT DOCUMENTS 5,322,055 A 6/1994 Davison et al.
5,776,155 A 7/1998 Beaupre et al.
(Continued)

FOREIGN PATENT DOCUMENTS

CN 105939679 A 9/2016
CN 106163430 A 11/2016
(Continued)

OTHER PUBLICATIONS

Brazilian Examination Report dated Feb. 17, 2022, for Application No. BR112019011694-0, 4 pages.
(Continued)

*Primary Examiner* — Michael F Peffley
*Assistant Examiner* — Amanda L Zink
(74) *Attorney, Agent, or Firm* — FBT Gibbons LLP

(57) ABSTRACT

A surgical instrument includes an end effector, a shaft assembly, and a torque wrench integrally connected with the shaft assembly. The shaft assembly has an acoustic waveguide extending therethrough and the end effector projects distally from the shaft assembly. The acoustic waveguide has a proximal end portion configured to rotatably couple with an ultrasonic transducer assembly. The torque wrench is configured to transmit torque applied to the acoustic waveguide up to a predetermined torque. A portion of the torque wrench is configured to deflect upon receipt of torque greater than the predetermined torque. Accordingly, the portion of the torque wrench slips relative to the acoustic waveguide for limiting coupling of the acoustic waveguide to the ultrasonic transducer assembly to the predetermined torque.

20 Claims, 15 Drawing Sheets

Related U.S. Application Data continuation of application No. 15/378,432, filed on Dec. 14, 2016, now Pat. No. 10,660,722.

(51) Int. Cl.

| | |
|---|---|
| ***A61B 90/00*** | (2016.01) |
| ***A61N 7/02*** | (2006.01) |
| *A61B 17/00* | (2006.01) |
| *A61B 18/00* | (2006.01) |

(52) U.S. Cl.

CPC ................. *A61B 2017/0046* (2013.01); *A61B 2017/00477* (2013.01); *A61B 2017/320069* (2017.08); *A61B 2017/320071* (2017.08); *A61B 2017/320094* (2017.08); *A61B 2017/320095* (2017.08); *A61B 2018/00345* (2013.01); *A61B 2018/00601* (2013.01); *A61B 2018/00619* (2013.01); *A61B 2018/0063* (2013.01); *A61B 2090/031* (2016.02)

(58) Field of Classification Search

CPC ....... A61B 2017/320071; A61B 2017/320094; A61B 2017/320095; A61B 2018/00345; A61B 2018/00601; A61B 2018/00619; A61B 2018/0063; A61B 2090/031; A61B 90/03

See application file for complete search history.

(56) References Cited

U.S. PATENT DOCUMENTS

| | | | |
|---|---|---|---|
| 5,873,873 A | 2/1999 | Smith et al. | |
| 5,897,523 A | 4/1999 | Wright et al. | |
| 5,980,510 A | 11/1999 | Tsonton et al. | |
| 5,989,264 A | 11/1999 | Wright | |
| 6,063,098 A | 5/2000 | Houser et al. | |
| 6,090,120 A | 7/2000 | Wright | |
| 6,325,811 B1 | 12/2001 | Messerly | |
| 6,454,782 B1 | 9/2002 | Schwemberger | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 | 8/2004 | Anderson et al. | |
| 7,135,030 B2 | 11/2006 | Schwemberger et al. | |
| 7,621,930 B2 | 11/2009 | Houser | |
| 8,461,744 B2 | 6/2013 | Wiener et al. | |
| 8,591,536 B2 | 11/2013 | Robertson | |
| 8,623,027 B2 | 1/2014 | Price et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,241,732 B2 | 1/2016 | Craig | |
| 9,381,058 B2 | 7/2016 | Houser et al. | |
| 9,393,037 B2 | 7/2016 | Olson et al. | |
| 9,402,682 B2 | 8/2016 | Worrell | |
| 9,408,622 B2 | 8/2016 | Stulen et al. | |
| 9,872,699 B2 | 1/2018 | Houser et al. | |
| 10,010,340 B2 | 7/2018 | Hibner et al. | |
| 10,172,636 B2 | 1/2019 | Stulen et al. | |
| 10,349,967 B2 | 7/2019 | Hibner et al. | |
| 10,660,722 B2 | 5/2020 | Lesko et al. | |
| D937,416 S * | 11/2021 | Funakoshi | D24/138 |
| 11,589,942 B2 | 2/2023 | Lesko et al. | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2012/0116265 A1 | 5/2012 | Houser et al. | |
| 2014/0107684 A1 * | 4/2014 | Craig | A61B 17/320092 29/428 |
| 2015/0245850 A1 * | 9/2015 | Hibner | A61B 17/320092 606/171 |
| 2015/0265309 A1 * | 9/2015 | Boudreaux | A61B 17/320092 606/169 |
| 2018/0161057 A1 | 6/2018 | Roberson et al. | |
| 2018/0161058 A1 | 6/2018 | Lesko | |
| 2018/0161060 A1 | 6/2018 | Roberson et al. | |

FOREIGN PATENT DOCUMENTS

| | | |
|---|---|---|
| JP | H02-261441 A | 10/1990 |
| JP | H03-501700 A | 4/1991 |
| WO | WO 2016/060835 A2 | 4/2016 |

OTHER PUBLICATIONS

Chinese Search Report dated Apr. 11, 2022, for Application No. 201780077809.6, 1 page.

European Communication dated Apr. 22, 2020, for Application No. 17817553.5, 6 pages.

Indian Examination Report dated Aug. 6, 2021, for Application No. 201917021463, 6 pages.

International Search Report and Written Opinion dated Feb. 13, 2018, for International Application No. PCT/US2017/063866, 11 pages.

Japanese Office Action and Search Report dated Sep. 28, 2021, for Application No. 2019-531819, 20 pages.

Korean Office Action dated Nov. 15, 2022, for Application No. 10-2019-7020369, 8 pages.

U.S. Appl. No. 61/410,603, entitled "Energy-Based Surgical Instruments," filed Nov. 5, 2010.

U.S. Appl. No. 62/176,880, entitled "Ultrasonic Surgical Device with Articulating End Effector," filed Apr. 22, 2014.

* cited by examiner

ULTRASONIC SURGICAL INSTRUMENT WITH INTEGRAL SHAFT ASSEMBLY TORQUE WRENCH

This application is a continuation of U.S. application Ser. No. 16/696,329, filed Nov. 26, 2019, and issued as U.S. Pat. No. 11,589,942 on Feb. 28, 2023, entitled "Ultrasonic Surgical Instrument with Integral Shaft Assembly Torque Wrench," which is a continuation of U.S. application Ser. No. 15/378,432, filed Dec. 14, 2016, and issued as U.S. Pat. No. 10,660,722 on May 26, 2020, entitled "Ultrasonic Surgical Instrument with Integral Shaft Assembly Torque Wrench."

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No.

2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006, the disclosure of which is incorporated by reference herein; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, entitled "Surgical Instruments with Articulating Shafts," now U.S. Pat. No. 9,393,037, issued Jul. 19, 2016, the disclosure of which is incorporated by reference herein; U.S. Pub. No. 2014/005703, entitled "Surgical Instruments with Articulating Shafts," published Jan. 2, 2014, now U.S. Pat. No. 9,408,622, issued Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, now U.S. Pat. No. 9,095,367, issued Aug. 4, 2015, the disclosure of which is incorporated by reference herein; U.S. Pub. No. 2015/0080924, entitled "Articulation Features for Ultrasonic Surgical Instrument," published Mar. 19, 2015, now U.S. Pat. No. 10,172,636, issued Jan. 8, 2019, the disclosure of which is incorporated by reference herein; and U.S. patent application Ser. No. 14/258,179, reverted to U.S. Provisional App. No. 62/176,880, entitled "Ultrasonic Surgical Device with Articulating End Effector," filed Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
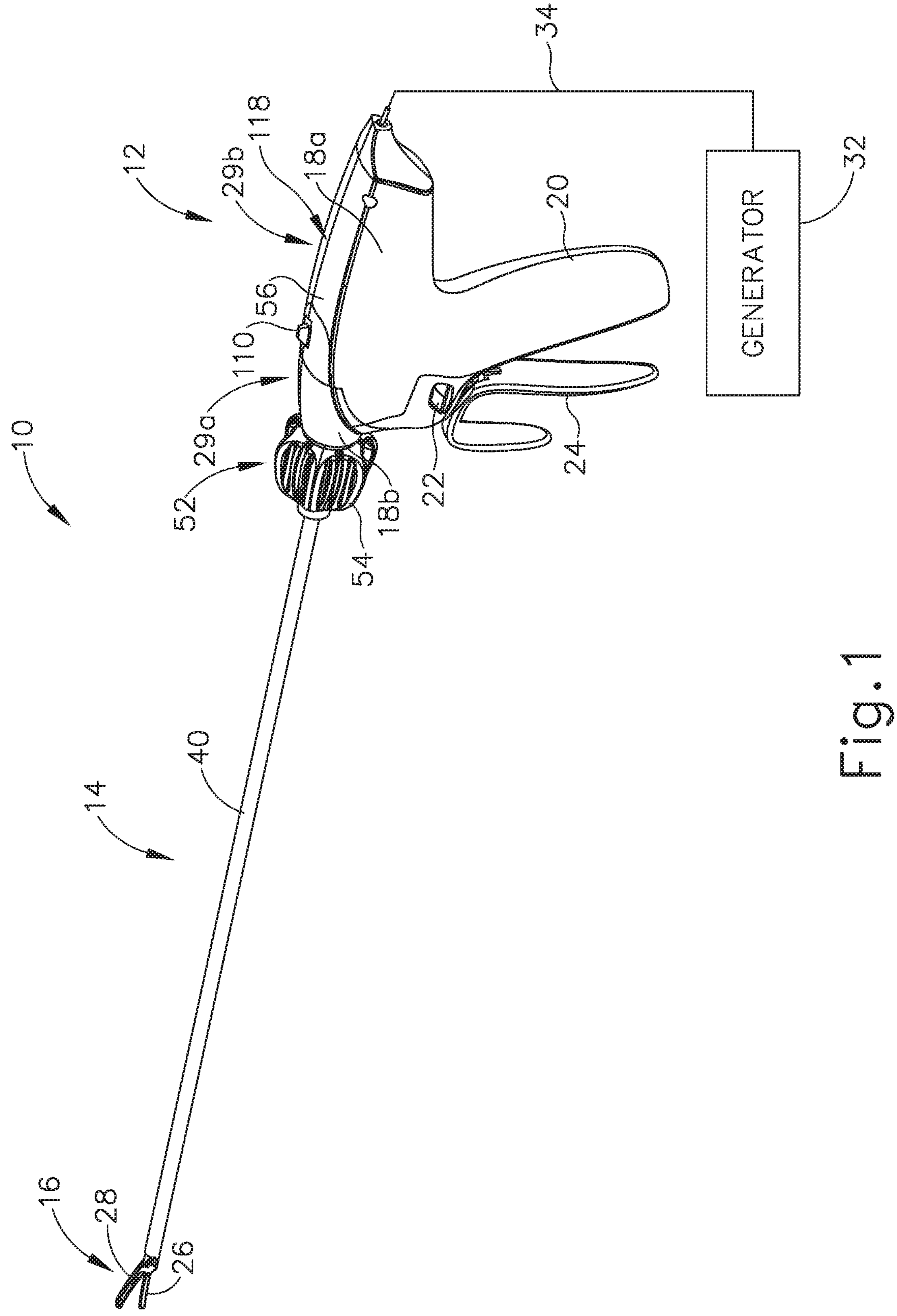
FIG. 1 depicts a perspective view of a first exemplary ultrasonic surgical instrument having a handle assembly, a shaft assembly, and an end effector.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that for convenience and clarity, spatial terms such as "upper," "lower," "inner," and "outer" are used herein with respect to the drawings. However, surgical instruments are used in many orientations and positions, and these terms are not intended to be limiting and absolute. The terms "proximal," "distal," "upper," "lower," "inner," and "outer" are thus relative terms and not intended to unnecessarily limit the invention described herein.

I. EXEMPLARY ULTRASONIC SURGICAL INSTRUMENT

FIG. 1 shows a first exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (12), a shaft assembly (14), and an end effector (16). Handle assembly (12) comprises a body (18*a*) including a pistol grip (20) and buttons (22). Handle assembly (12) also includes a trigger (24) that is pivotable toward and away from pistol grip (20). It should be understood, however, that various other suitable configurations may be used, including but not limited to a scissor grip configuration. End effector (16) includes an ultrasonic blade (26) and a pivoting clamp arm (28). Clamp arm (28) is coupled with trigger (24) such that clamp arm (28) is pivotable toward ultrasonic blade (26) in response to pivoting of trigger (24) toward pistol grip (20); and such that clamp arm (28) is pivotable away from ultrasonic blade (26) in response to pivoting of trigger (24) away from pistol grip (20). Various suitable ways in which clamp arm (28) may be coupled with trigger (24) will be apparent to those of ordinary skill in the art in view of the teachings herein. In some versions, one or more resilient members are used to bias clamp arm (28) and/or trigger (24) to the open position shown in FIG. 1.

Figure 2:
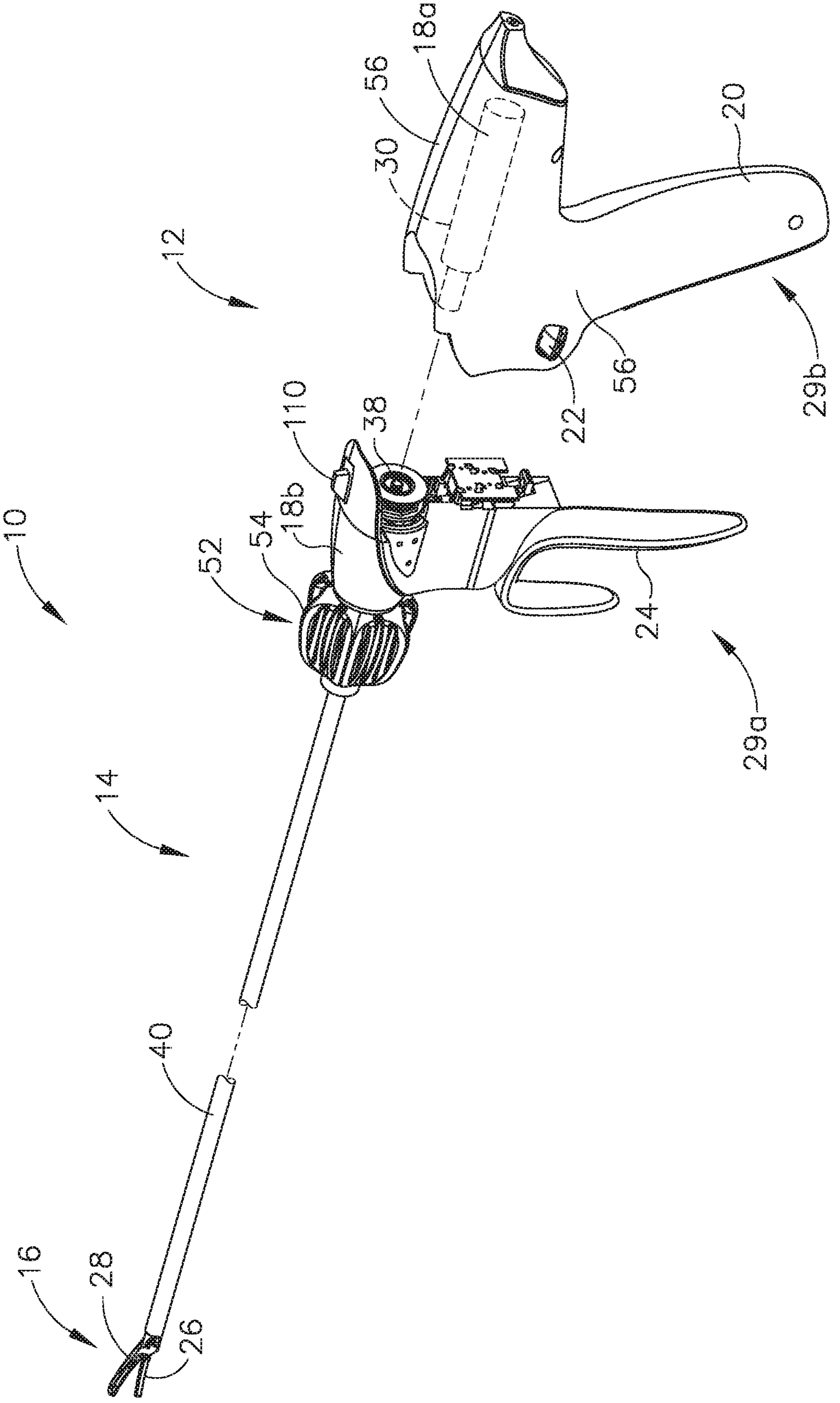
FIG. 2 depicts a partially exploded view of the ultrasonic surgical instrument of FIG. 1 with a disposable portion of the ultrasonic surgical instrument removed from a reusable portion of the ultrasonic surgical instrument.
Figure 6:
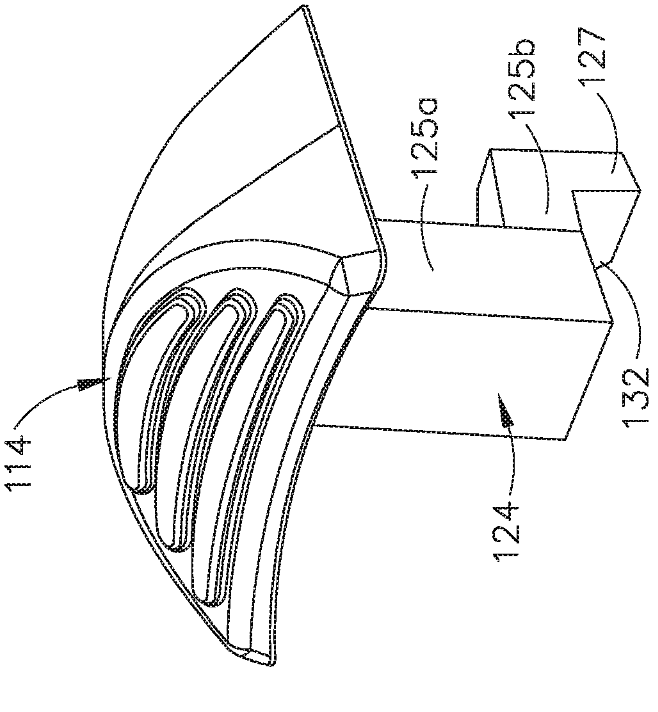
FIG. 6 depicts a perspective view of a lock switch of the integral slip lock of FIG. 4A.

Furthermore, instrument (10) of this example comprises a disposable assembly (29*a*) and a reusable assembly (29*b*) as illustrated in FIG. 2 in more detail. By way of example, disposable assembly (29*a*) generally includes shaft assembly (14), end effector (16), buttons (22), trigger (24), and a portion of body (18*b*), which may also be referred to herein as shaft assembly body (18*b*). By way of further example, reusable assembly (29*b*) generally includes the remaining portion of body (18*a*) with pistol grip (20) and an ultrasonic transducer assembly (30) (see FIG. 6A). To this end shaft assembly body (18*b*) and handle assembly body (18*a*) may collectively be referred to herein simply as body (18*a*, 18*b*). The distal portion of reusable assembly (29*b*) is configured to removably receive the proximal portion of disposable assembly (29*a*), as seen in FIGS. 1-2, to form instrument (10). To accommodate such disposable and reusable assemblies (29*a*, 29*b*), shaft assembly (14) and ultrasonic transducer assembly (30) (see FIG. 6A) are configured to removably couple together as will be discussed below in greater detail.

The ultrasonic transducer assembly (30) is positioned within body (18*a*) of handle assembly (12). Transducer assembly (30) is coupled with a generator (32) via a power cord (34), such that transducer assembly (30) receives electrical power from generator (32). Power cord (34) may also be referred to as cable (34) as described herein. Piezoelectric elements in transducer assembly (30) convert electrical power from generator (32) into ultrasonic vibrations. Generator (32) may include a power source and control module that is configured to provide a power profile to transducer assembly (30) that is particularly suited for the generation of ultrasonic vibrations through transducer assembly (30). By way of example only, generator (32) may comprise a GEN04 or GEN11 sold by Ethicon Endo-Surgery, Inc. of Cincinnati, Ohio. In addition, or in the alternative, generator (32) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (32) may be integrated into handle assembly (12), and that handle assembly (12) may even include a battery or other on-board power source such that cable (14) is omitted, while other cables may alternatively be used for electrically coupling various components. Still other suitable forms that generator (32) may take, as well as various features and operabilities that generator (32) may provide, will be apparent to those of ordinary skill in the art in view of the teachings herein.

In an exemplary use, assemblies (29*a*, 29*b*) are coupled together to form instrument (10) and then is used to perform the surgical procedure. Assemblies (29*a*, 29*b*) are then decoupled from each other for further processing. In some instances, after the surgical procedure is complete, disposable assembly (29*a*) is immediately disposed of while reusable assembly (29*b*) is sterilized and otherwise processed for re-use. By way of example only, reusable assembly (29*b*) may be sterilized in a conventional relatively low temperature, relatively low pressure, hydrogen peroxide sterilization process. Alternatively, reusable assembly (29*b*) may be sterilized using any other suitable systems and techniques. In some versions, reusable assembly (29*b*) may be sterilized and reused approximately 100 times. Alternatively, reusable assembly (29*b*) may be subject to any other suitable life cycle. For instance, reusable assembly (29*b*) may be disposed of after a single use, if desired. While disposable assembly (29*a*) is referred to herein as being "disposable," it should be understood that, in some instances, disposable assembly (29*a*) may also be sterilized and otherwise processed for re-use. By way of example only, disposable assembly (29*a*) may be sterilized and reused approximately 2-30 times, using any suitable systems and techniques. Alternatively, disposable assembly (29*a*) may be subject to any other suitable life cycle.

In some versions, disposable assembly (29*a*) and/or reusable assembly (29*b*) includes one or more features that are operable to track usage of the corresponding assembly (29*a*, 29*b*), and selectively restrict operability of the corresponding assembly (29*a*, 29*b*) based on use. For instance, disposable assembly (29*a*) and/or reusable assembly (29*b*) may include one or more counting sensors and a control logic (e.g., microprocessor, etc.) that is in communication with the counting sensor(s). The counting sensor(s) may be able to detect the number of times instrument (10) is activated, the number of surgical procedures the corresponding assembly (29*a*, 29*b*) is used in, and/or any other suitable conditions associated with use. The control logic may track data from the counting sensor(s) and compare the data to one or more threshold values. When the control logic determines that one or more threshold values have been exceeded, the control logic may execute a control algorithm to disable operability of one or more components in the corresponding assembly (29*a*, 29*b*). In instances where the control logic stores two or more threshold values (e.g., a first threshold for number of activations and a second threshold for number of surgical procedures, etc.), the control logic may disable operability of one or more components in the corresponding assembly (29*a*, 29*b*) the first time one of those thresholds is exceeded, or on some other basis.

In versions where a control logic is operable to disable instrument (10) based on the amount of use, the control logic may also determine whether instrument (10) is currently being used in a surgical procedure, and refrain from disabling instrument (10) until that particular surgical procedure is complete. In other words, the control logic may allow the operator to complete the current surgical procedure but prevent instrument (10) from being used in a subsequent surgical procedure. Various suitable forms that counters or other sensors may take will be apparent to those of ordinary skill in the art in view of the teachings herein. Various suitable forms that a control logic may take will also be apparent to those of ordinary skill in the art in view of the teachings herein. Similarly, various suitable control algorithms that may be used to restrict usage of instrument (10) will be apparent to those of ordinary skill in the art in view of the teachings herein. Of course, some versions of instrument (10) may simply omit features that track and/or restrict the amount of usage of instrument (10). Additional and/or alternative features with respect to alternative disposable and reusable assemblies (29*a*, 29*b*) may be constructed in accordance with at least some of the teachings of U.S. Pub. No. 2016/0015419, entitled "Ultrasonic Surgical Instrument with Removable Handle Assembly," published Jan. 21, 2016, now U.S. Pat. No. 10,349,967, issued Jul. 16, 2019, the disclosure of which is incorporated by reference herein. In any case the invention described herein is not intended to be limited to use with only replaceable or reusable components as described herein.

A. Exemplary End Effector and Shaft Assembly

Figure 3A:
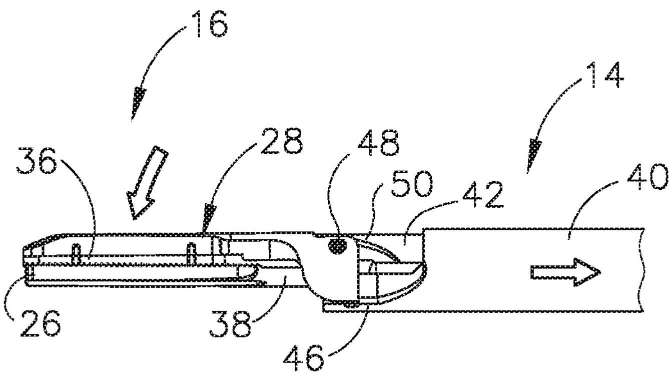
FIG. 3A depicts an enlarged side elevational view of the end effector of FIG. 1 in a closed position.
Figure 3B:
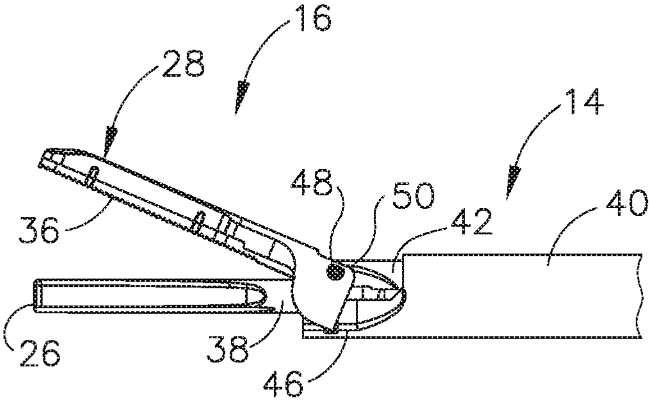
FIG. 3B depicts an enlarged side elevational view of the end effector of FIG. 1 in an open position.

As best seen in FIGS. 3A-3B, end effector (16) of this example comprises clamp arm (28) and ultrasonic blade (26) as discussed briefly above. Clamp arm (28) includes a clamp pad (36), which faces blade (26). Clamp arm (28) is pivotable toward and away from blade (26) to selectively compress tissue between clamp pad (36) and blade (26). More particularly, blade (26) is an integral feature of a distal end of an acoustic waveguide (38), which extends coaxially through tubes (40, 42), and which is configured to communicate ultrasonic vibrations to blade (26) as will be described in greater detail below.

Shaft assembly (14) comprises an outer tube (40) and an inner tube (42). Outer tube (40) is operable to translate longitudinally relative to inner tube (42) to selectively pivot clamp arm (28) toward and away from blade (26). To accomplish this, integral pin features (not shown) extending inwardly from respective projections (44) of clamp arm (28) pivotally secure a first portion of clamp arm (28) to a distally projecting tongue (46) of outer tube (40); while an inserted pin (48) pivotally secures a second portion of clamp arm (28) to a distally projecting tongue (50) of inner tube (42). Thus, tubes (40, 42) cooperate to pivot clamp arm (28) toward blade (26) when outer tube (40) is retracted proximally relative to inner tube (42). It should be understood that clamp arm (28) may be pivoted back away from blade (26) by translating outer tube (40) distally relative to inner tube (42). In an exemplary use, clamp arm (28) may be pivoted toward blade (26) to grasp, compress, seal, and sever tissue captured between clamp pad (36) and blade (26) as shown in FIG. 3A. Clamp arm (28) may also be pivoted away from blade (26), as shown in FIG. 3B, to release tissue from between clamp pad (36) and blade (26); and/or to perform blunt dissection of tissue engaging opposing outer surfaces of clamp arm (28) and blade (26). In some alternative versions, inner tube (42) translates while outer tube (40) remains stationary to provide pivotal movement of clamp arm (28).

As shown in FIGS. 1-2, shaft assembly (14) of the present example extends distally from handle assembly (12). A rotation control assembly (52) has rotation control member in the form of rotation control knob (54), which is secured to a proximal portion of outer tube (40). Knob (54) is rotatable relative to shaft assembly body (18*b*), such that shaft assembly (14) is rotatable about the longitudinal axis defined by outer tube (40), relative to handle assembly (12). Such rotation may provide rotation of end effector (16) and shaft assembly (14) unitarily, which also includes unitary rotation of acoustic waveguide (38) coupled with transducer assembly (30) within handle assembly (12). In some alternative versions, various rotatable features may simply be omitted and/or replaced with alternative rotatable features, if desired.

While the present shaft assembly (14) is generally rigid and linear, it will be appreciated that alternative shaft assemblies may include an articulation section (not shown) for deflecting end effector (16) at various lateral deflection angles relative to a longitudinal axis defined by outer tube (40). It will be appreciated that such an articulation section may take a variety of forms. By way of example only, an articulation section may be configured in accordance with one or more teachings of U.S. Pub. No. 2012/0078247, entitled "Articulation Joint Features for Articulation Surgical Device," published on Mar. 29, 2012, now U.S. Pat. No.

9,402,682, issued Aug. 2, 2016, the disclosure of which is incorporated by reference herein. As another merely illustrative example, an articulation section may be configured in accordance with one or more teachings of U.S. Pub. No. 2014/0005701, now U.S. Pat. No. 9,393,037, and/or U.S. Pub. No. 2014/0114334, now U.S. Pat. No. 9,095,367, the disclosures of which are incorporated by reference herein. Various other suitable forms that an articulation section may take will be apparent to those of ordinary skill in the art in view of the teachings herein.

B. Exemplary Handle Assembly

As seen in FIGS. 1 and 2, handle assembly (12) is reusable as discussed above and comprises body (18) defined by a pair of complementary housings (56) joined together. Housings (56) collectively define pistol grip (20) and may include a cord support base (not shown) through which cable (34) extends between transducer assembly (30) and generator (32). While body (18) includes pistol grip (20) in this example, it should be understood that any other suitable kind of grip may be used.

Waveguide (38) extends proximally through knob (54) and into body (18) to mechanically couple with transducer assembly (30). When waveguide (38) is sufficiently coupled with transducer assembly (30), ultrasonic vibrations that are generated by transducer assembly (30) are communicated along waveguide (38) to reach blade (26). By way of example, waveguide (38) is threadably received by transducer assembly (30) for acoustically coupling waveguide (38) to transducer assembly (30) for use. In order to properly communicate the resonant ultrasonic vibrations from transducer assembly (30) to waveguide (38), a predetermined torque is applied to waveguide (38) during installation with transducer assembly (30). In some versions, a torque wrench (not shown), separate from handle assembly (12) and shaft assembly (14) may be used to couple the waveguide (38) with the transducer assembly (30) to inhibit overtightening of the waveguide (38). By way of example only, such a torque wrench may be configured and operable in accordance with at least some of the teachings of U.S. Pub. No. 2007/0191713, entitled "Ultrasonic Device for Cutting and Coagulating," published Aug. 16, 2007, now abandoned, the disclosure of which is incorporated by reference herein.

In the present example, the distal end of blade (26) is located at a position corresponding to an anti-node associated with resonant ultrasonic vibrations communicated through waveguide (38), in order to tune the acoustic assembly to a preferred resonant frequency $f_o$ when the acoustic assembly is not loaded by tissue. When transducer assembly (30) is energized, the distal end of blade (26) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (30) of the present example is activated, these mechanical oscillations are transmitted through waveguide (38) to reach blade (26), thereby providing oscillation of blade (26) at the resonant ultrasonic frequency. Thus, when tissue is secured between blade (26) and clamp pad (36), the ultrasonic oscillation of blade (26) may simultaneously sever the tissue and denature the proteins in adjacent tissue cells, thereby providing a coagulative effect with relatively little thermal spread. In some versions, an electrical current may also be provided through blade (26) and/or clamp pad (36) to also seal the tissue.

Further exemplary features and operabilities for disposable and/or reusable portions of surgical instrument (10) will be described in greater detail below, while other variations will be apparent to those of ordinary skill in the art in view of the teachings.

II. SHAFT ASSEMBLY WITH INTEGRAL TORQUE WRENCH FOR COUPLING WAVEGUIDE WITH TRANSDUCER ASSEMBLY

As described above with respect to surgical instrument (10), once waveguide (38) and transducer assembly (30) are secured together at the predetermined torque, selective rotation of knob (54) collectively rotates the remainder of shaft assembly (14), end effector (16), waveguide (38), and transducer assembly (30) relative to handle assembly (12). However, even before proper installation at the predetermined torque, the proximal end of waveguide (38) may have enough frictional engagement with transducer assembly (30) to cause transducer assembly (30) to rotate with waveguide (38) relative to handle assembly (12). Such engagement may make it difficult, or even impossible in some cases, for a user to apply the predetermined torque for proper coupling of the waveguide (38) to transducer assembly (30), because the user may not be able to apply a reactionary torque to transducer assembly (30) up to the predetermined torque.

In order to facilitate coupling of waveguide (38) with transducer assembly (30), some versions of surgical instrument (10) may include a transducer lock. Various exemplary transducer locks are described in greater detail in U.S. patent application Ser. No. 15/378,414, entitled "Ultrasonic Surgical Instrument with Integral Torque Wrench and Transverse Engagement," filed on even date herewith, now U.S. Pat. Pub. No. 2018/0161058, published Jun. 14, 2018, the disclosure of which is incorporated by reference herein; U.S. patent application Ser. No. 15/378,452, entitled "Ultrasonic Surgical Instrument with Transducer Locking Feature," filed on even date herewith, now U.S. Pat. Pub. No. 2018/0161060, published Jun. 14, 2018, the disclosure of which is incorporated by reference herein; and U.S. patent application Ser. No. 15/378,391, entitled "Ultrasonic Surgical Instrument with Integral Torque Wrench and Longitudinal Engagement," filed on even date herewith, now U.S. Pat. Pub. No. 2018/0161057, published Jun. 14, 2018, the disclosure of which is incorporated by reference herein.

While a transducer lock may inhibit rotation of transducer assembly (30), the separate torque wrench (not shown) is applied to shaft assembly (14) in at least some of the above referenced examples for providing the predetermined torque while inhibiting overtightening of waveguide (38) with transducer assembly (30). However, handling and manipulating the torque wrench (not shown) separately from surgical instrument (10) adds further complexity to the surgical procedure and may be difficult to manage in some instances. Moreover, the torque wrench (not shown) may wear out over a number of uses and maintaining the torque wrench (not shown) to provide clear and accurate limitations on torque to the predetermined torque may also be difficult over time.

It may thus be desirable to integrate a torque wrench, or at least some of the features and operability of a torque wrench, into shaft assembly (14) of surgical instrument (10) in order to provide both torque limiting and transducer assembly seizing features. In the instance where shaft assembly (14) and an integral torque wrench are part of a disposable and replaceable portion of surgical instrument (10), the torque wrench would be essentially new for use in the surgical procedure, thereby reducing the desire to provide occasional maintenance to the torque wrench.

The following description relates to various exemplary torque wrenches (110, 210, 310, 410) integrated into shaft assemblies (14, 214) for use with surgical instruments (12, 212) discussed below in greater detail. Accordingly, like numbers described herein indicate like features with respect to each exemplary torque wrench (110, 210, 310, 410). While torque wrenches (110, 210, 310, 410) are configured to selectively inhibit, and even prevent rotation of transducer assembly (30) relative to body (18), in addition to limiting torque, it will be appreciated that some rotation in alternative examples is possible in accordance with the invention. For example, alternative torque wrenches may not strictly prevent rotation, but at least inhibit rotation enough to provide a reactionary torque equal to at least the predetermined torque for proper installation. The invention is thus not intended to be unnecessarily limited to preventing all relative rotation between transducer assembly (30) and body (18).

A. Exemplary Integral Slip Lock

FIGS. 1-2 and 4A-9B illustrate a first exemplary torque wrench, in the form of an integral slip lock (110) of surgical instrument (10), which is configured to both inhibit rotation of transducer assembly (30) and limit torque applied at the interface between transducer assembly (30) and waveguide (38) to the predetermined torque. As shown in FIGS. 4A-5A, slip lock (110) includes a lock switch (114) extending through a lock channel (116) in shaft assembly body (18*b*). More particularly, lock channel (116) extends longitudinally through an upper surface (118) of shaft assembly body (18*b*) directly above the longitudinal axis. Lock switch (114) is thus translatable between a distal, unlocked position and a proximal, locked position for respectively unlocking and locking rotation of transducer assembly (30) relative to shaft assembly body (18*b*). While lock switch (114) and lock channel (116) are positioned on upper surface (118) of shaft assembly body (18*b*) in the present example, it will be appreciated that lock switch (114) and lock channel (116) may be alternatively positioned to cooperate with transducer assembly (30). The invention is thus not intended to be unnecessarily limited to having lock switch (114) and lock channel (116) positioned as shown herein.

Figure 4B:
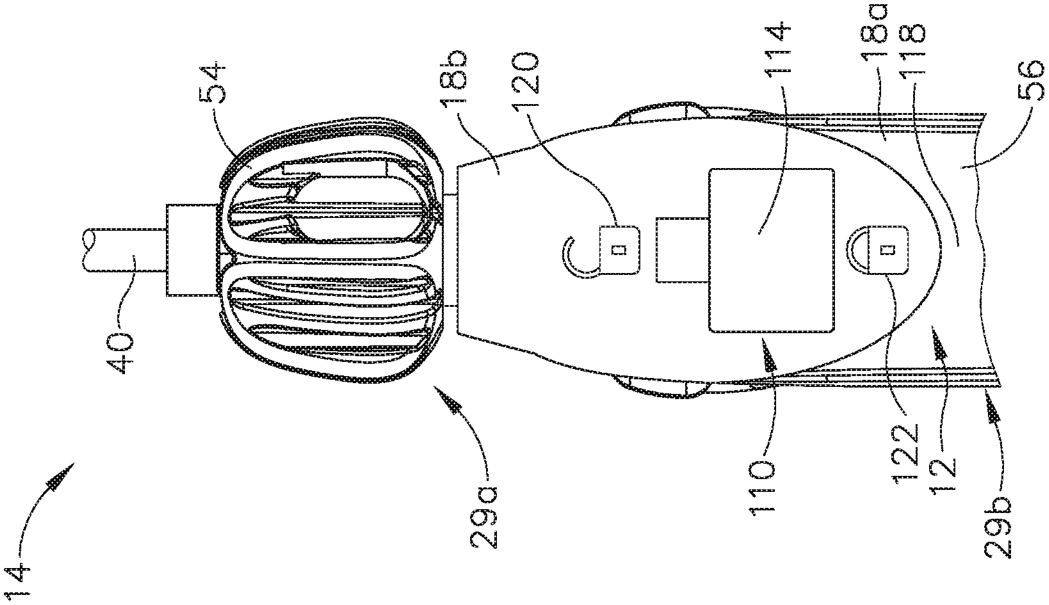
FIG. 4B depicts the enlarged top view of the integral slip lock of FIG. 4A in a locked position.
Figure 4A:
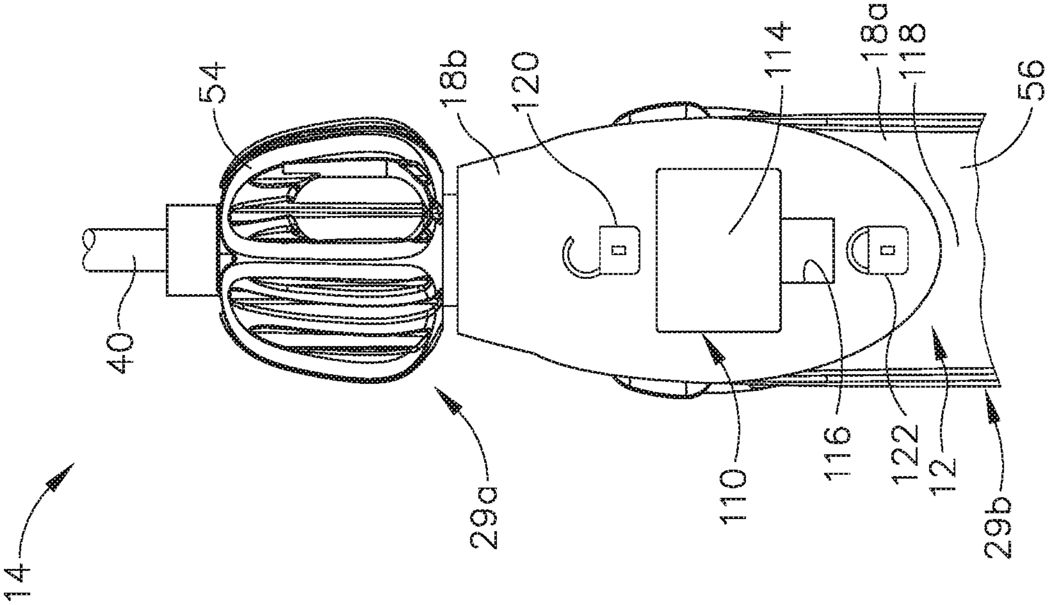
FIG. 4A depicts an enlarged top view of an integral slip lock of the ultrasonic surgical instrument of FIG. 1 in an unlocked position.

As seen in FIGS. 4A-4B, upper surface (118) further includes an unlocked indicia (120) and a locked indicia (122) for visually indicating a rotational state (i.e., unlocked state or locked state) of transducer assembly (30) to the user. The present example has unlocked indicia (120) positioned adjacent to a distal end of lock channel (116), whereas locked indicia (122) is positioned adjacent to a proximal end of lock channel (116). Unlocked indicia (120) more particularly includes an image of an unlocked padlock, and locked indicia (122) more particularly includes an image of a locked padlock. However, it will be appreciated that these particular images and positions may vary in accordance with the invention herein and should not be unnecessarily limited to these particular unlocked and locked indicia (120, 122). Furthermore, slip lock (110) may also include one or more cooperating detents (not shown) to releasably secure lock switch (114) in either of the unlocked and locked positions. The user may then manipulate other portions of surgical instrument (112) without necessarily holding lock switch (114) in the locked position. In some variations, lock switch (114) may be biased toward the unlocked position such that the user would hold lock switch (114) in the locked position while coupling with waveguide (38). The invention is thus not intended to be unnecessarily limited to either secured or biased lock switch (114) positions.

As seen in FIGS. 5A-7, slip lock (110) further includes an arrester (124) operatively connected to lock switch (114) and an engagement feature (126) operatively connected to transducer assembly (30). Arrester (124) and engagement feature (126) are configured to cooperate with each other to selectively allow or inhibit rotation of transducer assembly (30) relative to body (18). To this end, arrester (124) extends transversely downwardly from lock switch (114) toward the longitudinal axis and, in the unlocked position, is distally offset from engagement feature (126) and transducer assembly (30). More particularly, as shown in FIGS. 5B-7, arrester (124) includes a downward stem (125*a*) extending transversely downwardly from lock switch (114) and a longitudinal stem (125*b*) extending proximally from downward stem (125*a*) to a catch cam (127). Catch cam (127) is configured to deflect relative to engagement feature (127) upon application of torque greater than the predetermined torque at waveguide (38) to release engagement feature (127) for limiting torque to the predetermined torque. In the present example, stems (125*a*, 125*b*) are resiliently connected, with longitudinal stem (125*b*) being configured to deflect upward relative to transverse stem (125*a*). However, it will be appreciated that catch cam (127) may be directed to move via alternative deflection of another portion of slip lock (110). The invention is thus not intended to be unnecessarily limited to the particular deflection between stems (125*a*, 125) described herein.

Engagement feature (126) of the present example is particularly in the form of an engagement collar (126) having an annular collar body (128) and a plurality of teeth (130) positioned angularly about annular collar body (128). Each tooth (130) extends radially outwardly from annular collar body (128) such that any pair of teeth (130) is configured to receive catch cam (127) of arrester (124) therebetween. Furthermore, engagement collar (126) is rigidly secured to a distal end portion of transducer assembly (30) and positioned concentrically about the longitudinal axis. Engagement collar (126) is thus rotatably fixed relative to transducer assembly (30) such that each may either rotate together relative to body (18*a*, 18*b*) or be rotatably secured together relative to body (18*a*, 18*b*).

Figure 5A:
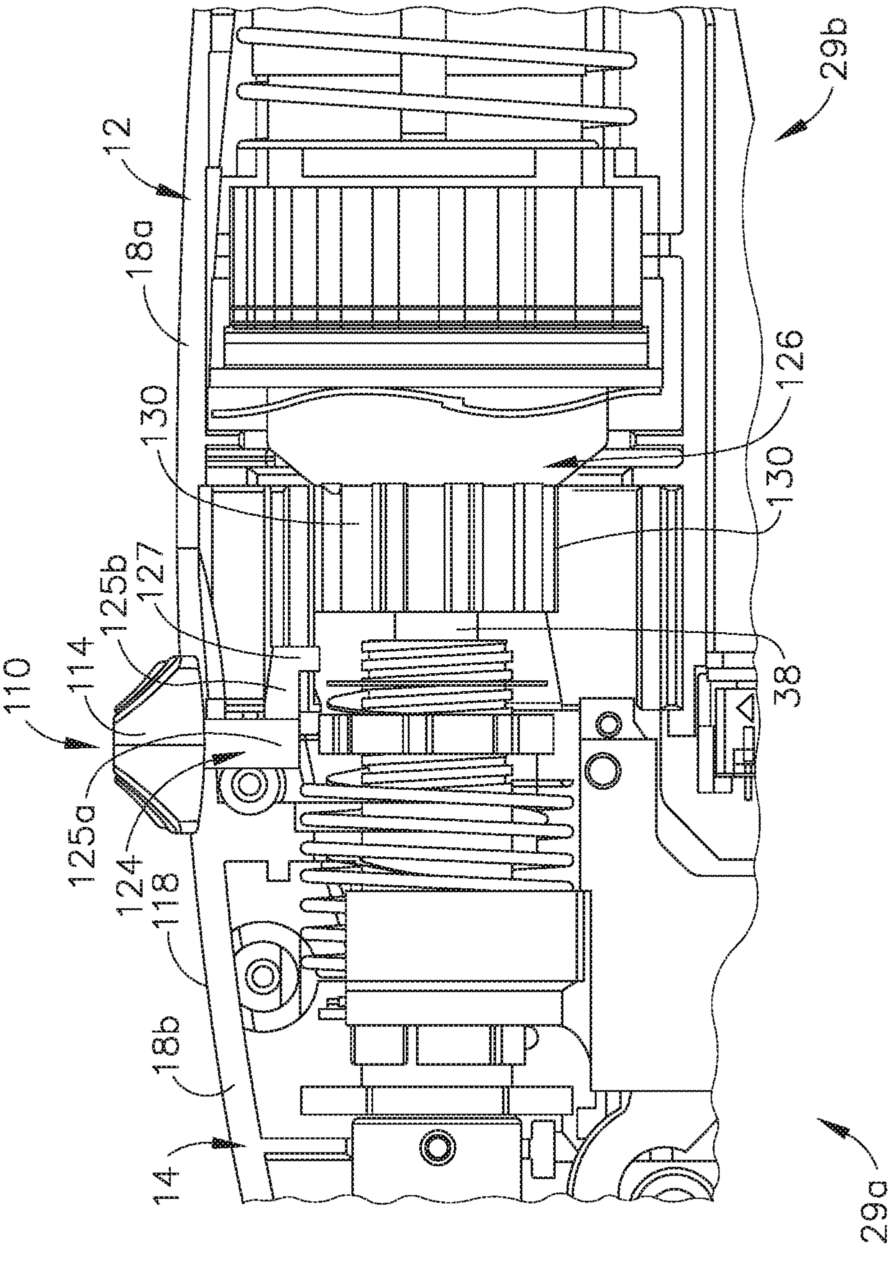
FIG. 5A depicts an enlarged side elevational view of the integral slip lock of FIG. 4A in the unlocked position, having various components removed for clarity.
Figure 5B:
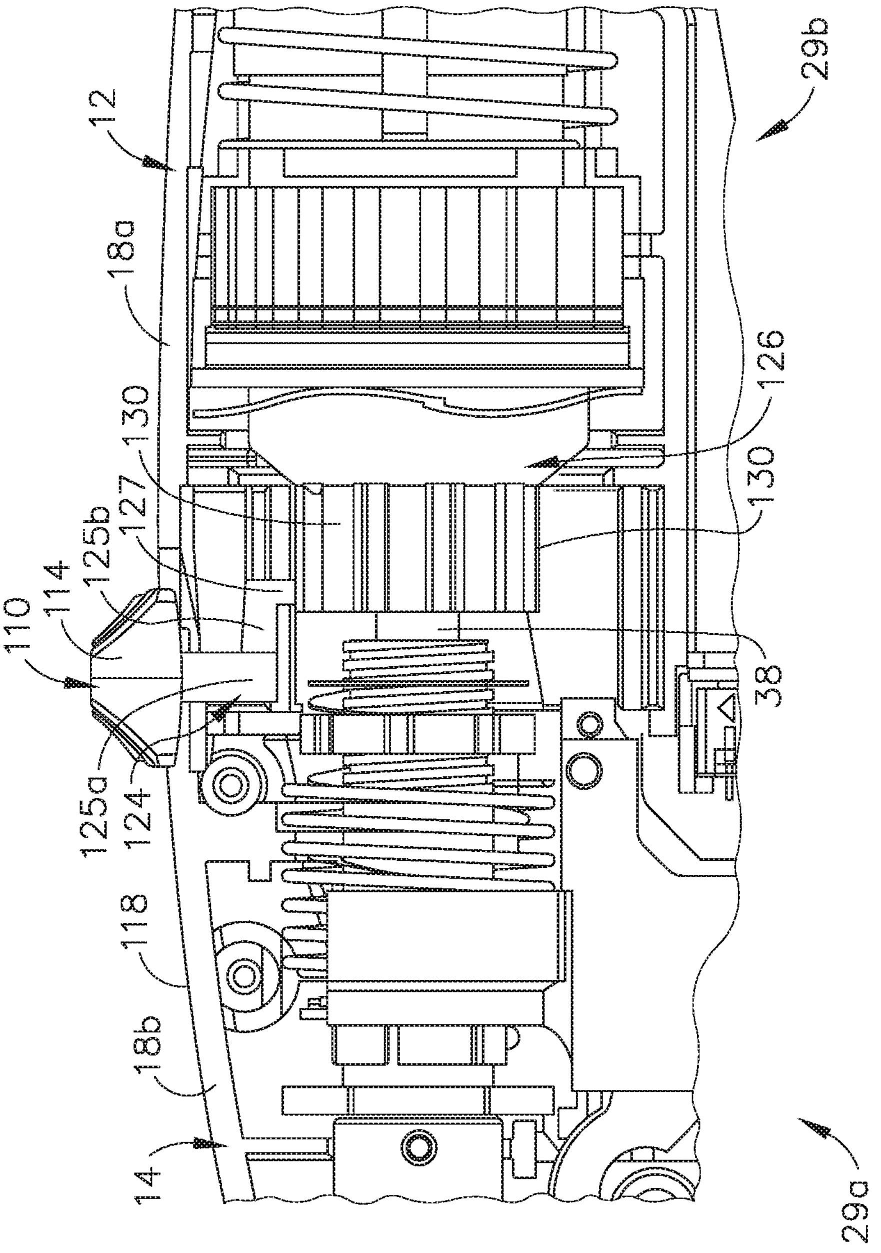
FIG. 5B depicts an enlarged side elevational view of the integral slip lock of FIG. 4B in the locked position, having various components removed for clarity.
Figure 7:
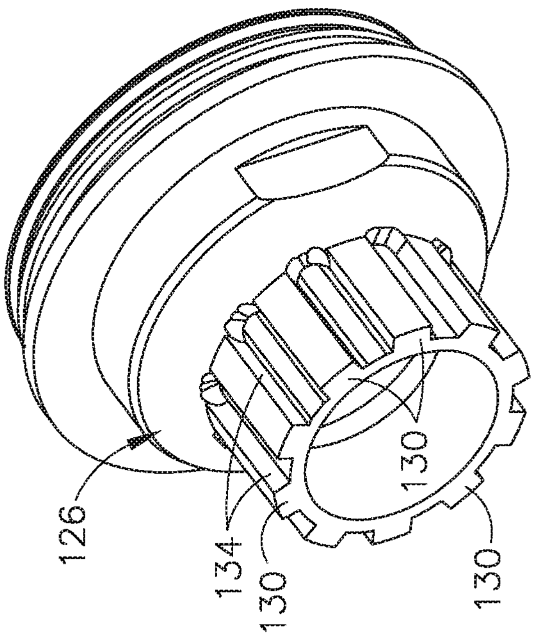
FIG. 7 depicts a perspective view of an engagement collar of the ultrasonic surgical instrument of FIG. 1.
Figure 8A:
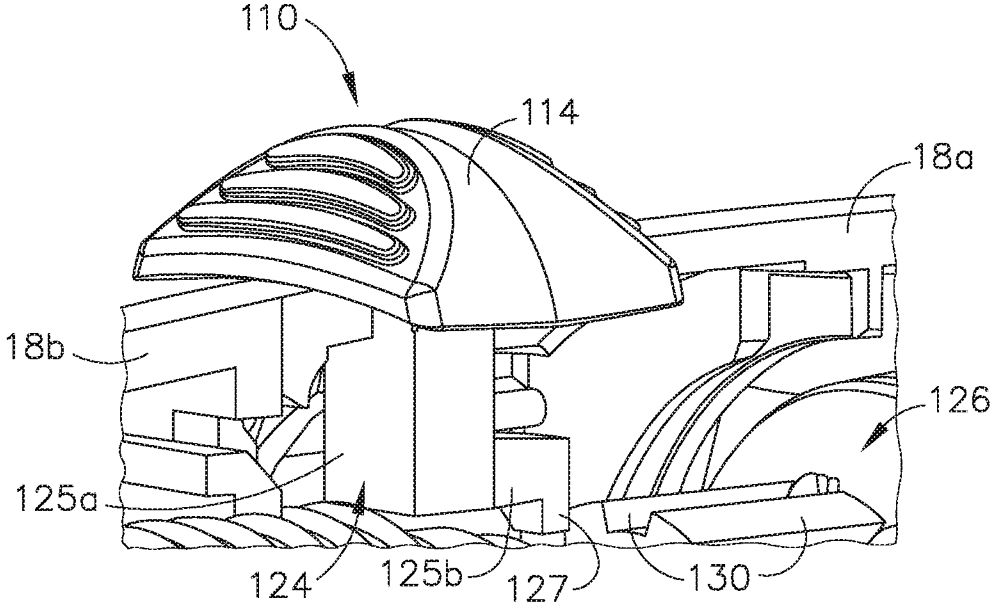
FIG. 8A depicts a perspective view of the lock switch of FIG. 4A disengaged from the engagement collar of FIG. 7, providing an integral torque wrench assembly in an unlocked state.
Figure 8B:
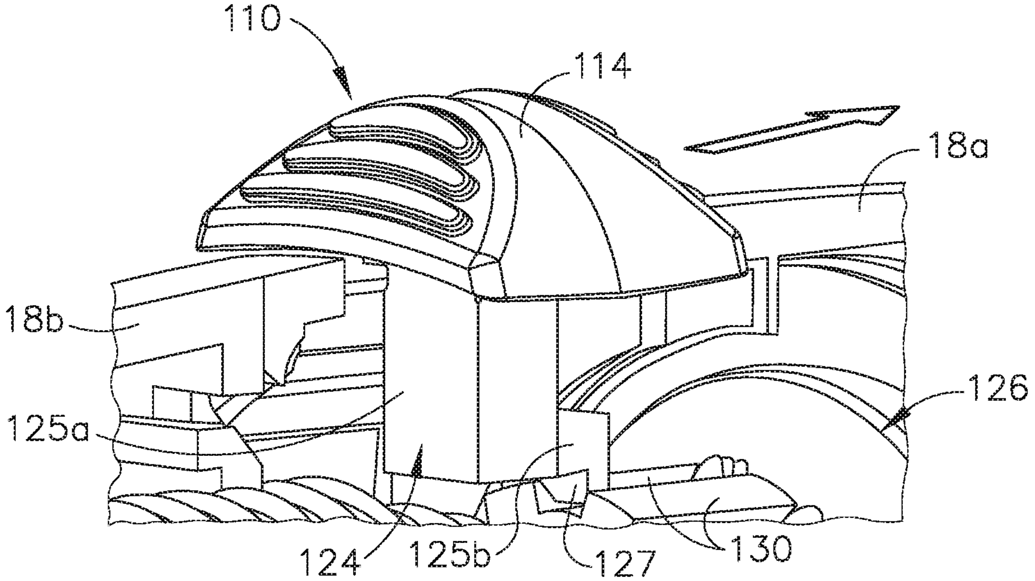
FIG. 8B depicts a perspective view of the lock switch of FIG. 4A engaged with the engagement collar of FIG. 7, providing an integral torque wrench assembly in a locked state.

FIGS. 5A and 8A illustrate lock switch (114) in the distal, unlocked position with arrester (124) in a distal, disengaged position, offset from engagement collar (126). Proximally translating lock switch (114) from the unlocked position toward the locked position similarly translates arrester (124) proximally from the disengaged position toward the engaged position shown in FIGS. 5B and 8B. In the engaged position, cam catch (127) of arrester (124) radially aligns between teeth (130) such that arrester (124) effectively engages teeth (130) to seize rotation of engagement collar (126) relative to body (18*a*, 18*b*). In turn, engagement collar (126) inhibits further rotation of transducer assembly (30) relative to body (18).

Figure 9B:
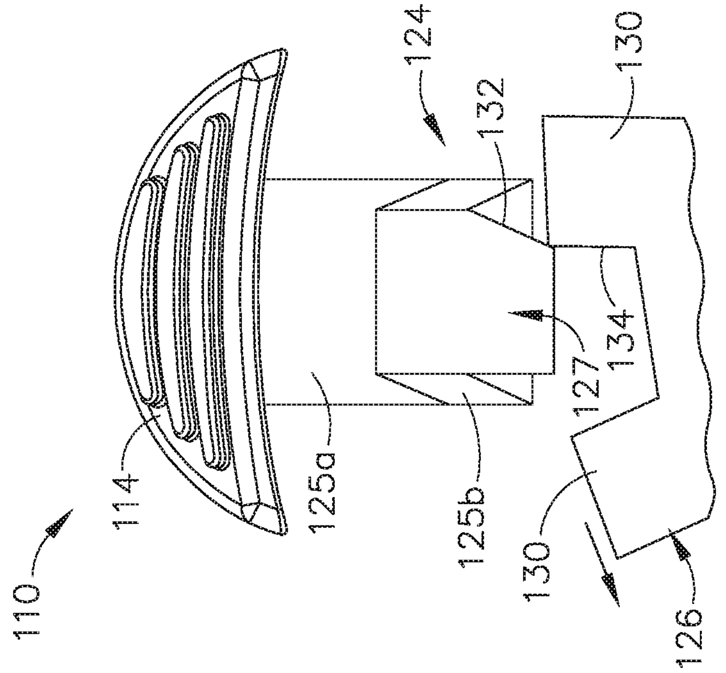
FIG. 9B depicts a rear elevational view of the lock switch of FIG. 4A engaged with the engagement collar of FIG. 7 in a manner to release rotation of the engagement collar at a predetermined torque.
Figure 9A:
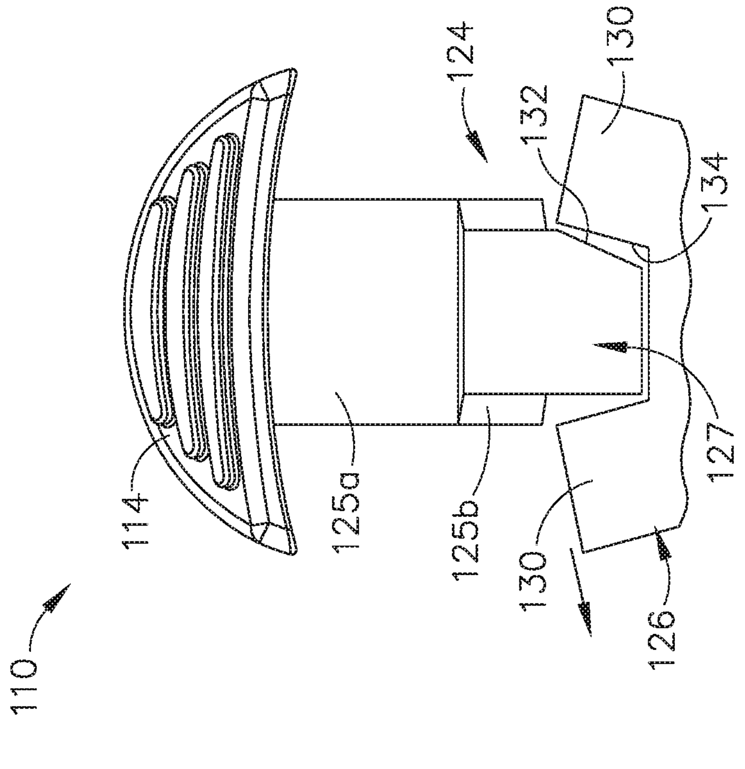
FIG. 9A depicts a rear elevational view of the lock switch of FIG. 4A engaged with the engagement collar of FIG. 7 in a manner to inhibit rotation of the engagement collar.

In addition, as shown in FIGS. 9A-9B, catch cam (127) has a driven cam surface (132), while each tooth (130) has a drive cam surface (134). Driven and drive cam surfaces (132, 134) cooperate such that drive cam surface (134) rotates against driven cam surface (134) to seize engagement collar (126) with arrester (124) as shown in FIG. 9A. However, as the applied torque increases while coupling waveguide (38) (see FIG. 5B) with transducer assembly (30) toward the predetermined torque, drive cam surface (134) of engagement collar (126) directs driven cam surface (132) upward about the deflection between stems (125*a*, 125*b*). So long as drive and driven cam surfaces (134, 132) remain engaged with catch cam (127) between teeth (130), engagement collar (126) remains seized relative to arrester (124) and body (18*a*, 18*b*) for tightening waveguide (38) (see FIG. 5B). Once the applied torque increases beyond the predetermined torque as shown in FIG. 9B, the relative deflection between stems (125*a*, 125*b*) is configured to lift catch cam (127) from engagement collar (126) such that catch cam (127) rotatably releases engagement collar (126). In turn, engagement collar (126) rotatably slips relative to catch cam (127) to inhibit overtightening of waveguide (38) (see FIG. 5B) with transducer assembly (30) (see FIG. 5B) beyond the predetermined torque.

In use, shaft assembly (14) with integrally connected slip lock (110) is initially uncoupled from transducer assembly (30). The user translates lock switch (114) of slip lock (110) proximally from the unlocked position to the locked position such that catch cam (127) of arrester (124) engages engagement collar (126) to seize rotation of transducer assembly (30) relative to body (18*a*, 18*b*). The user then introduces the proximal end portion of waveguide (38) into threaded hole (62) and rotates knob (54) in a tightening direction to threadably engage the proximal end portion of waveguide (38) with transducer assembly (30). Even as frictional engagement between the waveguide (38) and transducer assembly (30) increases, in turn increasing applied torque, arrester (124) continues to block rotation of teeth (130) on engagement collar (126). The user thus continues to tighten waveguide (38) into transducer assembly (30) until reaching the predetermined torque. As applied torque increases, catch cam (127) eventually deflects upwardly until reaching the predetermined torque and, in turn, releases engagement collar (126) for relative slippage to prevent overtightening of waveguide (38). Catch cam (127) of the present example resiliently returns downwardly between another pair of teeth (130) and, in the event that torque continues to be applied, will continue to deflect and slip to prevent overtightening of waveguide (38). The user then distally translates lock switch (114) to withdraw arrester (124) from engagement collar (126) such that waveguide (38) and transducer assembly (30) may be collectively rotated unitarily via knob (54) during the surgical procedure.

By way of further example, slippage of catch cam (127) relative to teeth (130) and the resilient return of catch cam (127) downwardly to its original position may also generate an audible indicator, a tactile indicator, or other signal to the user that waveguide (38) is coupled with transducer assembly (30) at the predetermined torque. Slip lock (110) may thus also provide an integral torque indicator for indicating to the user that waveguide (38) has been coupled to the transducer assembly (30) with the predetermined torque.

B. First Exemplary Integral Knob Slip Assembly

Figure 10:
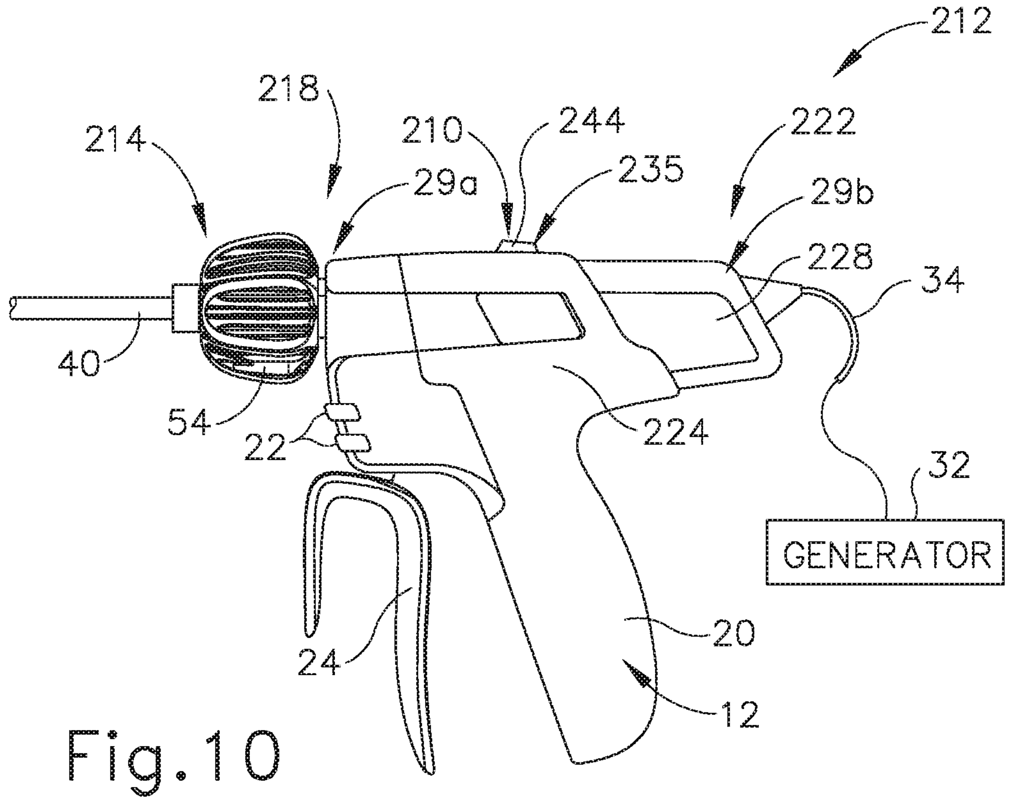
FIG. 10 depicts a side elevational view of a second exemplary ultrasonic surgical instrument having a handle assembly and a shaft assembly.
Figure 11:
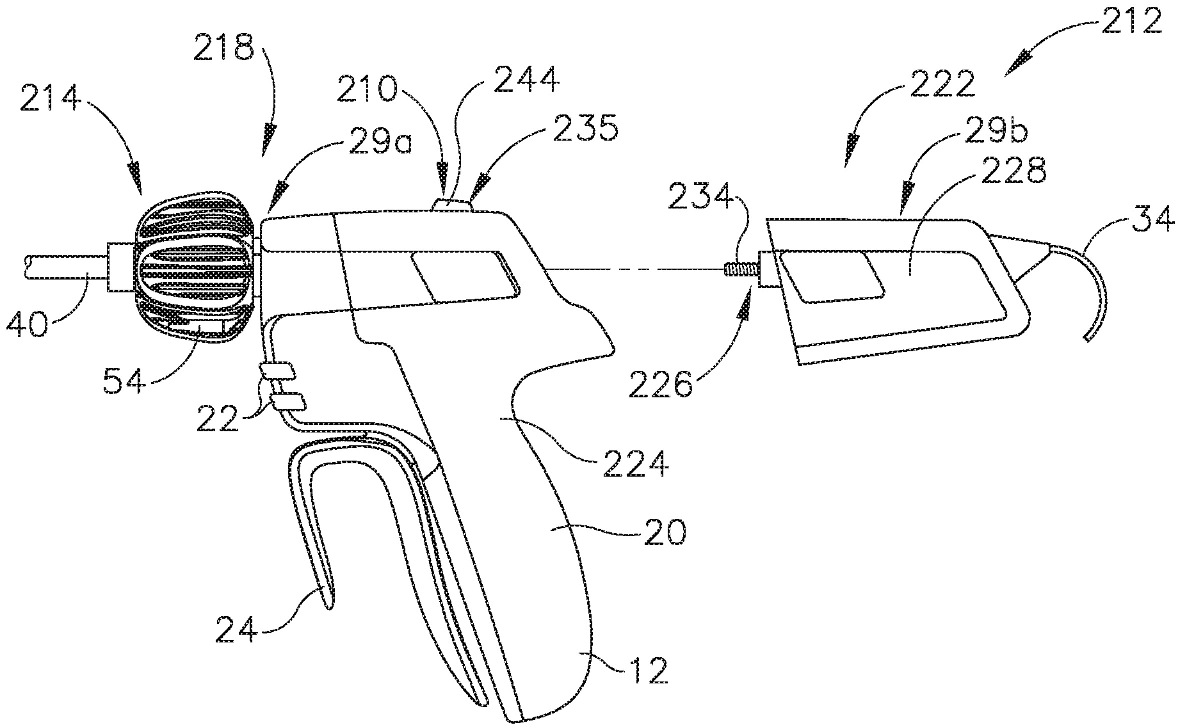
FIG. 11 depicts a partially exploded side elevational view of the ultrasonic surgical instrument of FIG. 10.
Figure 12:
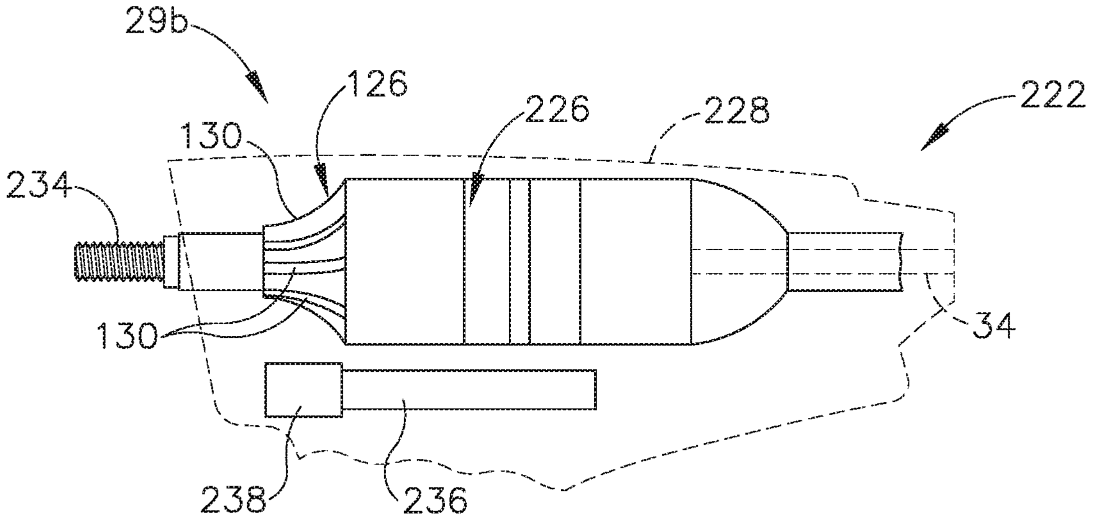
FIG. 12 depicts a partial side elevational view of a proximal portion of the handle assembly of FIG. 10 having various components removed for clarity with respect to an ultrasonic transducer assembly.

As seen in FIGS. 10-12, a second ultrasonic surgical instrument (212) includes a distal portion (218) and a proximal portion (222). Distal portion (218) has a shaft assembly (214) with knob (54) and waveguide (38), end effector (16) (see FIG. 1), buttons (22), trigger (24) and a portion of a body (224), at least a portion of which may also be referred to as shaft assembly body (224). Shaft assembly (214) more particularly includes a second exemplary torque wrench feature in the form of a first exemplary knob slip assembly (210) described below in more detail. Proximal portion (222) generally includes pistol grip (20), a transducer assembly (226) contained within a cover (228) for storage and protection. Accordingly, cover (228) may also be considered a remaining portion of body (224) of surgical instrument (212). One or both of distal and proximal portions (218, 222) of surgical instrument (212) may be disposable and/or reusable as discussed above with respect to surgical instrument (10) (see FIG. 1). In the present example, distal portion (218) is disposable, whereas proximal portion (222) is reusable.

Figure 13:
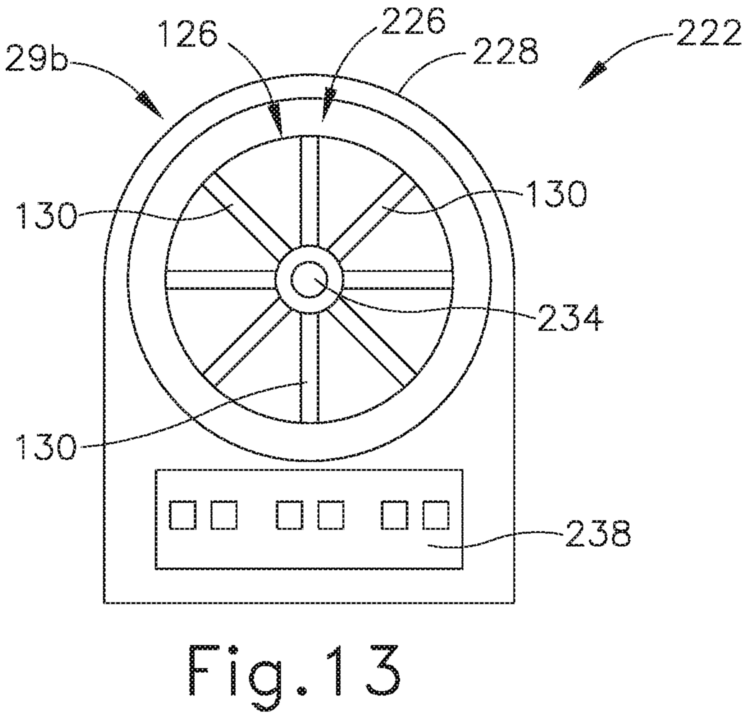
FIG. 13 depicts a distal end view of the proximal portion of the handle assembly of FIG. 10 having the ultrasonic transducer assembly.

FIGS. 11-13 illustrate proximal portion (222) in greater detail. In the present example, waveguide (38) (see FIG. 14A) has a threaded hole (232) coaxially positioned therein, whereas transducer assembly (226) has a threaded stud (234) configured to be threadably received within threaded hole (232) for coupling. In addition, proximal portion (222) also includes engagement collar (126) connected to transducer assembly (226) and configured to be selectively engaged by a transducer lock (235) for inhibiting rotation of transducer assembly (226) as discussed above in greater detail. Lower than transducer assembly (226) within cover (228), a circuit board (236) and electrical connector (238) are configured to electrically connect to distal portion (218) for electrical communication therebetween during the surgical procedure.

Figure 14A:
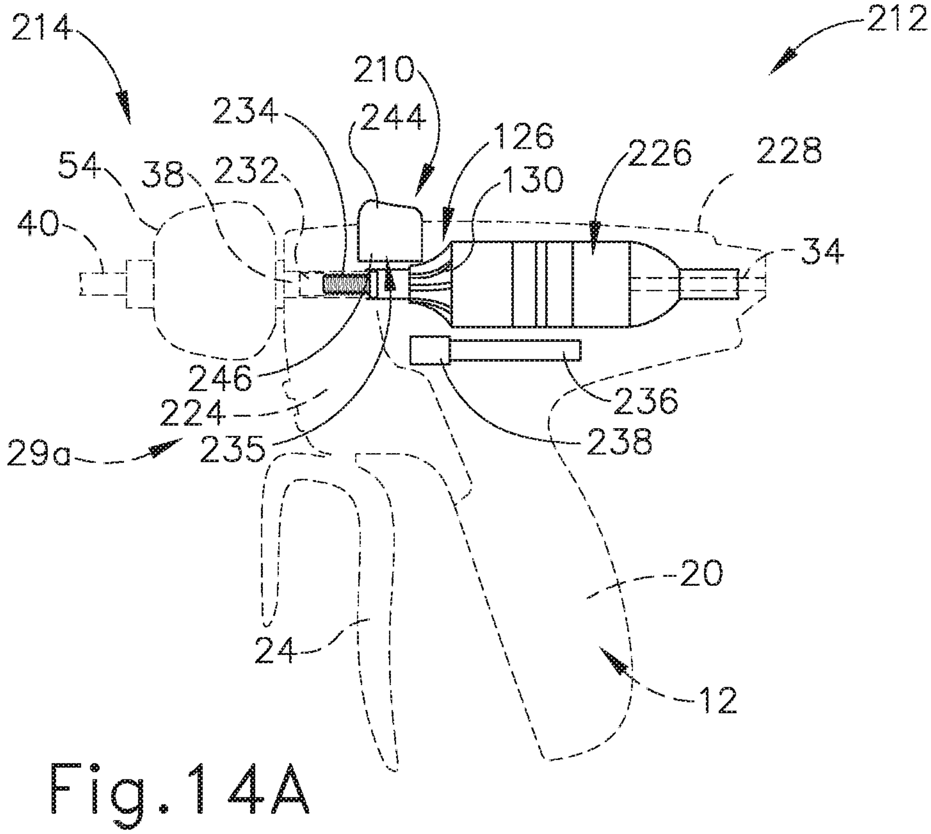
FIG. 14A depicts a side elevational view of the ultrasonic surgical instrument of FIG. 10, but having various components removed for clarity and a longitudinal catch lock in an unlocked position.
Figure 14B:
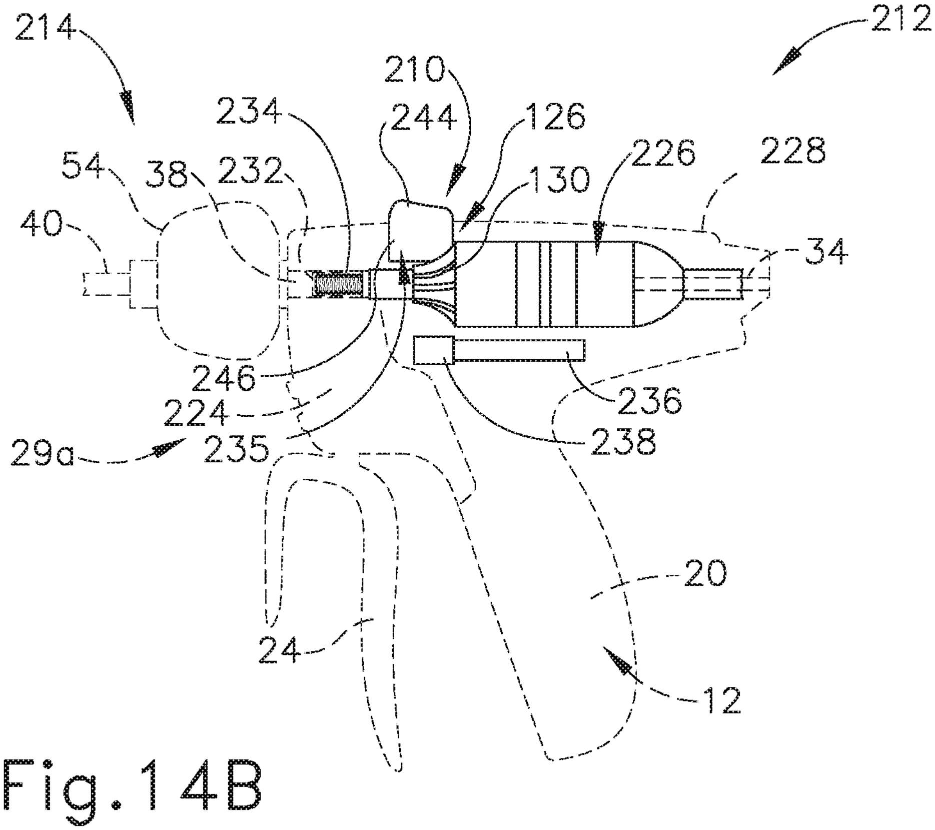
FIG. 14B depicts a side elevational view of the ultrasonic surgical instrument of FIG. 10, but having various components removed for clarity and the longitudinal catch lock in a locked position.

Knob slip assembly (210) generally includes a transducer lock (235) and a torque limiter (242) as shown in FIG. 14A-14B. Transducer lock (235) includes a lock switch (244) and an arrester (246) extending downwardly therefrom. Lock switch (244) is movable between unlocked and locked positions as discussed above with respect to lock switch (114) (see FIG. 5A-5B), while arrester (246) is similarly movable between disengaged and engaged positions as again discussed above with respect to arrester (124) (see FIG. 5A-5B). Arrester (246) is generally rigid and, rather than having a portion deflect like arrester (124), simply engages teeth (130) of engagement collar to inhibit rotation of transducer assembly (226) for coupling with waveguide (38) as shown in the locked position of FIG. 14B. The following thus describes torque limiter (242) in additional detail with lock switch (244) in the locked position to enable such coupling. It will be appreciated that alternative transducer locks may be similarly used with torque limiter (242). Accordingly, the invention is not intended to be unnecessarily limited to use with transducer lock (235) shown and described herein.

Figure 15A:
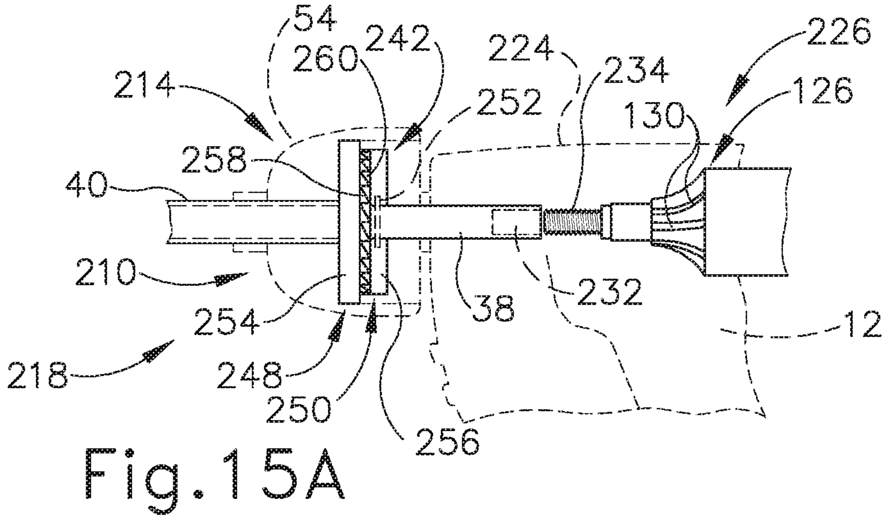
FIG. 15A depicts an enlarged side elevational view of the shaft assembly of FIG. 10 with a first integral knob slip assembly and the ultrasonic transducer assembly of FIG. 14B in the locked position.
Figure 15B:
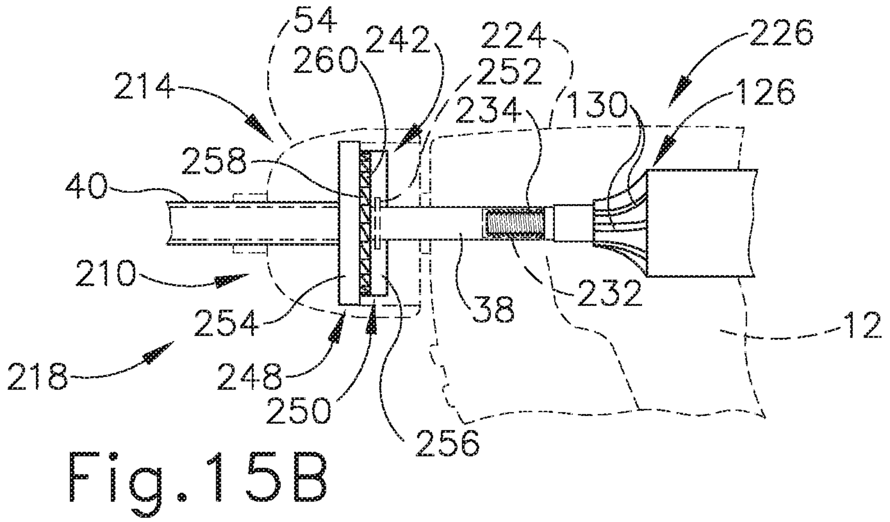
FIG. 15B depicts an enlarged side elevational view of the shaft assembly of FIG. 10 and the first integral knob slip assembly of FIG. 15A, with the shaft assembly coupling with the ultrasonic transducer assembly.
Figure 15C:
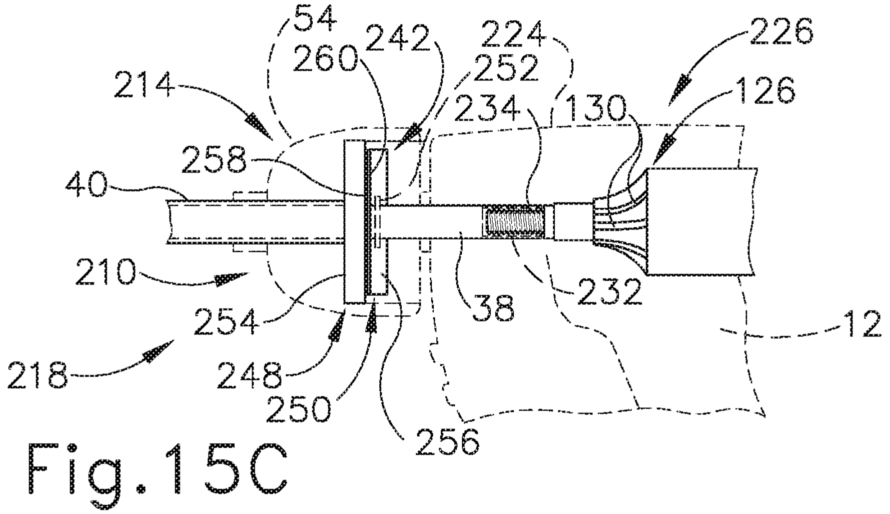
FIG. 15C depicts an enlarged side elevational view of the shaft assembly of FIG. 10 and the first integral knob slip assembly of FIG. 15A, with the shaft assembly slipping relative to the ultrasonic transducer assembly upon coupling therebetween.

As seen in FIGS. 15A-15C, torque limiter (242) in one example is integrated into knob (54) and includes a drive feature (248) that is configured to releasably engage a driven feature (250) and transmit torque therethough up to the predetermined torque for coupling waveguide (38) with transducer assembly (226). Drive feature (248) is rotatably secured, directly or indirectly, to knob (54) such that selectively rotating knob (54) similarly rotates drive feature (248). In the present example, drive feature (248) is directly connected to knob (54), with each being rotatable about the longitudinal axis. In contrast, driven feature (250) is rotatably secured, directly or indirectly, to waveguide (38) such that rotation of driven feature (250) similarly rotates waveguide (38) for coupling. In the present example, driven feature (250) is directly connected to waveguide (38) via a pin (252) at one of the nodes along waveguide (38) and is rotatable about the longitudinal axis.

By way of example, drive and driven features (248, 250) respectively include a drive disc (254) and a driven disc (256). Drive disc (254) is distally positioned within knob (54) relative to driven disc (256) such that drive disc (254) abuts against driven disc (256), which is also within knob (54). Each drive and driven disc (254, 256) has a central hole (not shown) extending therethrough configured to receive waveguide (38). With waveguide (38) in hole (not shown), drive disc (254) is configured to rotate about waveguide (38). However, pin (252) secures waveguide (38) to driven disc (256) to prevent such relative rotation.

Drive disc (254) further has a plurality of drive face teeth (258) extending proximally therefrom. Similarly, driven disc (256) has a plurality of driven face teeth (260) extending distally from driven disc (256) to releasably engage with drive face teeth (258). More particularly, drive face teeth (258) mesh with driven face teeth (260) to cooperatively transmit torque between drive and driven discs (258, 260). Each drive and driven face tooth (258, 260) of the present example is configured to resiliently deflect as the torque transmitted therethrough increases toward the predetermined torque for coupling waveguide (38) with transducer assembly (226) as shown in FIG. 15B. Once the torque at threaded stud (234) increases beyond the predetermined torque, drive and driven face teeth (258, 260) cooperatively deflect, such as by compression, and slip by each other. So long as the torque applied is greater than the predetermined torque, drive disc (254) will continue to slip relative to driven disc (256) to prevent torque at threaded stud (234) from increasing beyond the predetermined torque as shown in FIG. 15C. Once the applied torque drops below the predetermined torque, drive and driven face teeth (258, 260) resiliently return to releasably engage each other to transmit torque therethrough. While each of drive and driven teeth (258, 260) are shown deflecting in FIG. 15C, it will be appreciated that more or fewer portions of drive and driven features (248, 250) that releasably engage may deflect. For example, one of drive and driven features (248, 250) may be rigid and releasably engage with a deflectable portion of the other of drive and driven features (248, 250). The invention is thus not intended to be unnecessarily limited to each releasably engaging feature also being deflectable so long as drive feature (248) is configured to slip relative to driven feature (250).

In use, shaft assembly (214) with integrally connected knob slip assembly (210) is initially uncoupled from transducer assembly (226). The user translates lock switch (244) of transducer lock (235) proximally from the unlocked position to the locked position such that arrester (246) engages engagement collar (126) to seize rotation of transducer assembly (226) relative to body (224). The user then introduces threaded stud (234) of transducer assembly (226) into threaded hole (232) on waveguide (38) and rotates knob (54) in a tightening direction to threadably engage the proximal end portion of waveguide (38) with transducer assembly (226). The user continues to tighten waveguide (38) into transducer assembly (30) until reaching the predetermined torque. As applied torque increases, drive and driven face teeth (258, 260) deflect until reaching the predetermined torque and, in turn, drive face teeth (254) release driven face teeth (260) for relative slippage between drive and driven discs (254, 256) to inhibit overtightening of waveguide (38). Drive and driven face teeth (254, 256) of the present example resiliently return and, in the event that torque continues to be applied, will continue to deflect and slip to inhibit overtightening of waveguide (38). Once waveguide (38) is coupled with transducer assembly (226) with the predetermined torque, the user distally translates lock switch (2414) to withdraw arrester (246) from engagement collar (126) such that waveguide (38) and transducer assembly (30) may collectively rotate together. Drive and driven teeth (258, 260) remain releasably engaged to transmit torque such that the user may selectively rotate knob (54) to simultaneously rotate waveguide (38) and transducer assembly (226) during the surgical procedure. While the above use is described with respect to knob slip assembly (210) of surgical instrument (212), it will be appreciated that similar features of alternative knob slip assemblies (310, 410) may be similarly used for preparing surgical instruments (312, 412) for use during a surgical procedure.

By way of further example, slippage of drive and driven discs (254, 256) and the resilient return of drive and driven teeth (258, 260) against each other may also generate an audible indicator, a tactile indicator, or other signal to the user that waveguide (38) is coupled with transducer assembly (226) at the predetermined torque. Knob slip assembly (210) may thus also provide an integral torque indicator for indicating to the user that waveguide (38) has been coupled to the transducer assembly (226) with the predetermined torque.

C. Second Exemplary Integral Knob Slip Assembly

Figure 16A:
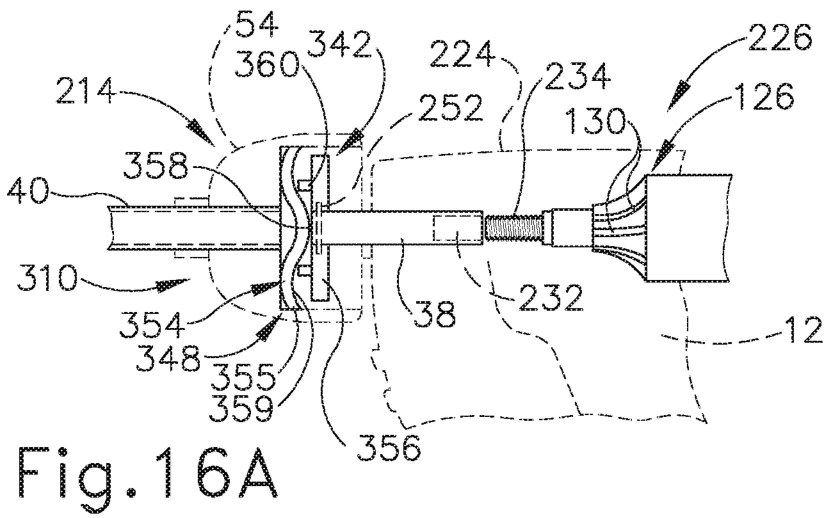
FIG. 16A depicts an enlarged side elevational view of the shaft assembly of FIG. 10 with a second integral knob slip assembly and the ultrasonic transducer assembly of FIG. 14B in the locked position.
Figure 16B:
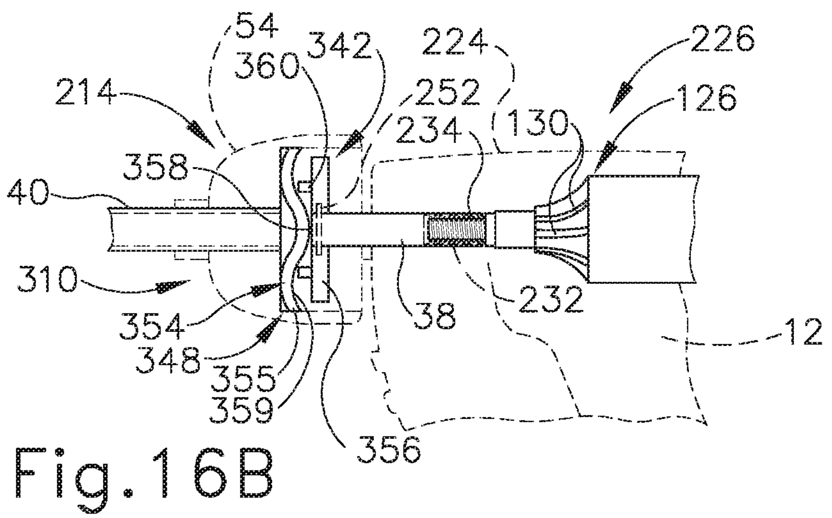
FIG. 16B depicts an enlarged side elevational view of the shaft assembly of FIG. 10 and the second integral knob slip assembly of FIG. 16A, with the shaft assembly coupling with the ultrasonic transducer assembly.
Figure 16C:
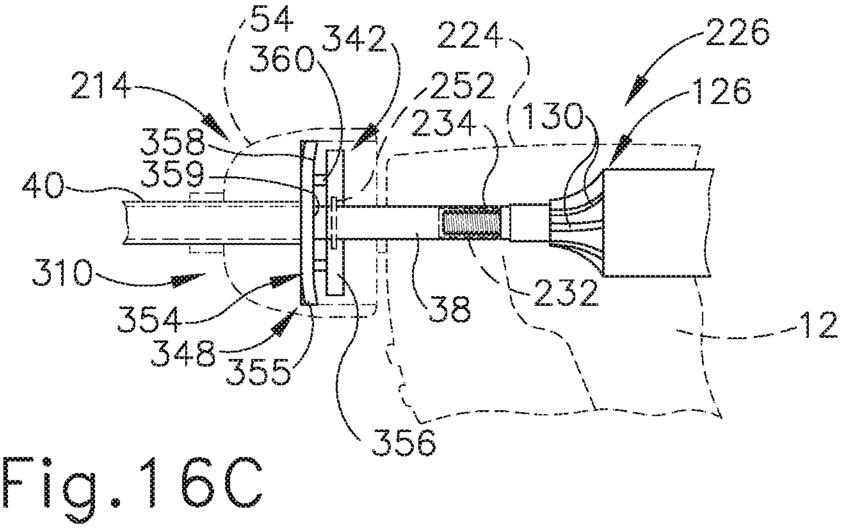
FIG. 16C depicts an enlarged side elevational view of the shaft assembly of FIG. 10 and the second integral knob slip assembly of FIG. 16A, with the shaft assembly slipping relative to the ultrasonic transducer assembly upon coupling therebetween.

As seen in FIGS. 16A-16C, a second integral knob slip assembly (310) includes a torque limiter (342) integrated into knob (54) and includes a drive feature (348) configured to releasably engage a driven feature (350) and transmit torque therethrough up to the predetermined torque for coupling waveguide (38) with transducer assembly (226). Drive feature (348) is rotatably secured, directly or indirectly, to knob (54) such that selectively rotating knob (54) similarly rotates drive feature (348). In the present example, drive feature (348) is directly connected to knob (54) with each being rotatable about the longitudinal axis. In contrast, driven feature (350) is rotatably secured, directly or indirectly, to waveguide (38) such that rotation of driven feature (350) similarly rotates waveguide (38) for coupling.

By way of example, drive and driven features (348, 350) respectively include a drive disc (354), which has a wave spring (355), and a driven disc (356). Drive disc (354) with wave spring (355) is distally positioned within knob (54) relative to driven disc (356) such that wave spring (355) abuts against driven disc (356), which is also within knob (54). Each drive and driven disc (354, 356) and wave spring (355) has a central hole (not shown) extending therethrough configured to receive waveguide (38). With waveguide (38) in hole (not shown), drive disc (354) with wave spring (355) is configured to rotate about waveguide (38). However, pin (252) secures waveguide (38) to driven disc (356) to prevent such relative rotation. In the present example, pin (252) is located at a position corresponding to a node associated with resonant ultrasonic vibrations communicated through waveguide (38).

Wave spring (355) generally defines a series of proximally facing peaks and valleys (358, 359). Driven disc (356) has a plurality of projections (360) extending distally from driven disc (356) to releasably engage with peaks (358) of wave spring (355). More particularly, peaks and valleys (358, 359) of wave spring (355) mesh with projections (360) such that each projection (360) is received within one respective valley (359) to cooperatively transmit torque between drive and driven discs (358, 360). Wave spring (355) of the present example is configured to resiliently deflect in the distal direction as the torque transmitted therethrough increases toward the predetermined torque for coupling waveguide (38) with transducer assembly (226) as shown in FIG. 16B. Once the torque at threaded stud (234) increases beyond the predetermined torque, projections (360) slip along wave spring (355) to compress wave spring (355). Once enough compression of wave spring (355) causes projections (360) to clear respective peaks (258), driven disc (354) further slips relative to drive disc (356). So long as the torque applied is greater than the predetermined torque, drive disc (354) will continue to slip relative to driven disc (356) to inhibit torque at threaded stud (234) from increasing beyond the predetermined torque as shown in FIG. 15C. Once the applied torque drops below the predetermined torque, wave spring (355) resiliently returns to releasably engage projections (360) to transmit torque therethrough.

By way of further example, slippage of drive and driven discs (354, 356) and the resilient return wave spring (355) against projections (360) may also generate an audible indicator, a tactile indicator, or other signal to the user that waveguide (38) is coupled with transducer assembly (226) at the predetermined torque. Knob slip assembly (310) may thus also provide an integral torque indicator for indicating to the user that waveguide (38) has been coupled to the transducer assembly (226) with the predetermined torque.

D. Third Exemplary Integral Knob Slip Assembly

Figure 17A:
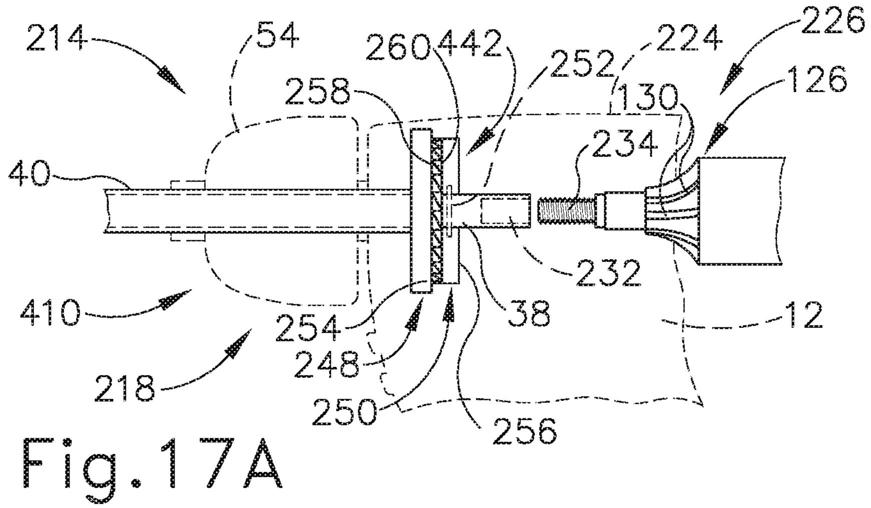
FIG. 17A depicts an enlarged side elevational view of the shaft assembly of FIG. 10 with a third integral knob slip assembly and the ultrasonic transducer assembly of FIG. 14B in the locked position.
Figure 17B:
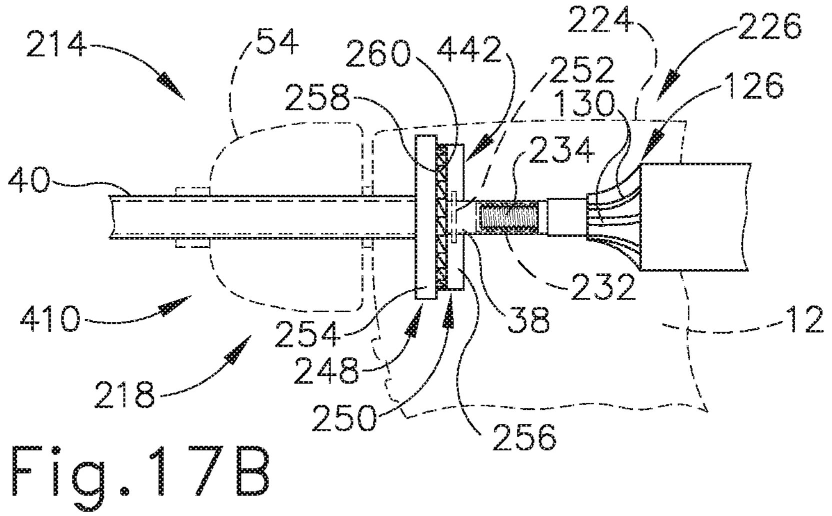
FIG. 17B depicts an enlarged side elevational view of the shaft assembly of FIG. 10 and the third integral knob slip assembly of FIG. 17A, with the shaft assembly coupling with the ultrasonic transducer assembly.
Figure 17C:
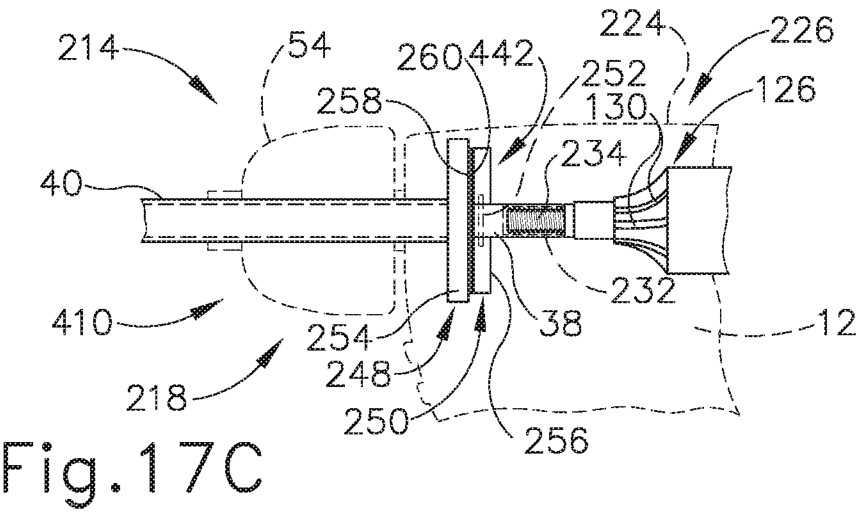
FIG. 17C depicts an enlarged side elevational view of the shaft assembly of FIG. 10 and the third integral knob slip assembly of FIG. 17A, with the shaft assembly slipping relative to the ultrasonic transducer assembly upon coupling therebetween.

As seen in FIGS. 17A-17C, a third integral knob slip assembly (410) includes a torque limiter (442) having drive and driven discs (254, 256) with releasably engaging drive and driven face teeth (258, 260) as discussed above in greater detail. To this end, integral knob slip assembly (410) generally operates similar to first integral knob slip assembly (210) (see FIG. 15A). However, drive disc (254) is directly connected to tube (40), which is rigidly connected to knob (54). In other words, drive disc (254) is rotatably secured relative to knob (54) via tube (40).

Tube and drive disc (254) extend proximally from knob (54) to driven disc (256), which is rotatably secured by pin (252) at another nodal position. Accordingly, drive and driven discs (254, 255), which are integrated with shaft assembly (214), project proximally from the remainder of shaft assembly (214). In some versions, drive and drive discs (254, 256) may be positioned within an alternative handle assembly, such as handle assembly (12) (see FIG. 1), while extending from shaft assembly (214). It will be appreciated that integral knob slip assembly (410) may be alternatively positioned relative to the remainder of shaft assembly, and the invention is not intended to be unnecessarily limited to particular location of knob slip assembly (410) shown in FIGS. 17A-17C.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an end effector; (b) a shaft assembly having an acoustic waveguide extending therethrough, wherein the end effector projects distally from the shaft assembly, and wherein the acoustic waveguide has a proximal end portion configured to rotatably couple with an ultrasonic transducer assembly; and (c) a torque wrench integrally connected with the shaft assembly and configured to transmit torque applied to the acoustic waveguide up to a predetermined torque, wherein a portion of the torque wrench is configured to deflect upon receipt of torque greater than the predetermined torque such that the portion of the torque wrench slips relative to the acoustic waveguide for limiting coupling of the acoustic waveguide to the ultrasonic transducer assembly to the predetermined torque.

Example 2

The surgical instrument of Example 1, wherein the torque wrench further includes a lock member configured to be selectively moved from an unlocked position to a locked position, wherein the lock member in the unlocked position is configured to allow rotation of the ultrasonic transducer assembly, and wherein the lock member in the locked position is configured to seize the ultrasonic transducer assembly for selectively inhibiting rotation thereof for rotatably coupling with the acoustic waveguide.

Example 3

The surgical instrument of Example 2, wherein the shaft assembly further includes a shaft assembly body having a switch channel, wherein the lock member includes a lock switch movably mounted in the lock channel, and wherein the lock switch is configured to be manipulated by a user between the locked and unlocked positions.

Example 4

The surgical instrument of Example 3, wherein the torque wrench further includes an arrester operatively connected to the lock switch and configured to selectively move between a disengaged position and an engaged position as the lock switch is respectively moved between the unlocked position and the locked position, wherein the arrester is configured to engage an engagement feature connected to the ultrasonic transducer assembly for inhibiting rotation of the ultrasonic transducer assembly.

Example 5

The surgical instrument of Example 4, wherein the arrester is the portion of the torque wrench configured to deflect upon receipt of torque greater than the predetermined torque.

Example 6

The surgical instrument of Example 5, further comprising: (a) an instrument body; and (b) an ultrasonic transducer assembly configured to rotatably couple with the proximal end portion of the acoustic waveguide, wherein the ultrasonic transducer assembly is rotatably mounted along a longitudinal axis within the instrument body such that the ultrasonic transducer assembly is configured to selectively rotate about the longitudinal axis, wherein the engagement feature is connected to the ultrasonic transducer assembly such that inhibiting rotation of the engagement feature thereby inhibits rotation of the ultrasonic transducer assembly.

Example 7

The surgical instrument of Example 6, wherein the engagement feature includes an engagement collar connected to the ultrasonic transducer assembly and positioned concentrically about the longitudinal axis, wherein the engagement collar has a plurality of teeth positioned angularly about the engagement collar, and wherein the arrester is configured to be received between the plurality of teeth in the engaged position to rotatably engage the engagement collar thereby inhibiting rotation of the engagement collar and the ultrasonic transducer assembly connected thereto up to the predetermined torque.

Example 8

The surgical instrument of any one or more of Examples 1 through 7, wherein the shaft assembly further includes a selectively rotatable knob having the acoustic waveguide extending therethrough, wherein the torque wrench is operatively coupled between the acoustic waveguide and the knob and configured to transmit torque from the knob to the acoustic waveguide up to the predetermined torque, wherein the portion of the torque wrench is configured to deflect upon receipt of torque greater than the predetermined torque and slip such that the knob rotates relative to the acoustic waveguide for limiting coupling of the acoustic waveguide to the ultrasonic transducer assembly to the predetermined torque.

Example 9

The surgical instrument of Example 8, wherein the torque wrench further includes a drive feature rotatably secured relative to the knob and a driven feature rotatably secured relative to the acoustic waveguide, wherein the drive feature is engaged with the driven feature to transmit torque thereto up to the predetermined torque, and wherein the drive feature is configured to slip relative to the driven feature upon receiving torque greater than the predetermined torque for limiting torque transition to the driven feature.

Example 10

The surgical instrument of Example 9, wherein the drive feature includes a drive disc and the drive feature includes a driven disc, and wherein the drive and driven discs are positioned coaxially with the acoustic waveguide.

Example 11

The surgical instrument of Example 10, wherein the drive disc includes a plurality of drive face teeth facing proximally, wherein the driven disc includes a plurality of driven face teeth facing distally and rotatably secured with the plurality of drive face teeth up to the predetermined torque, wherein at least a portion of the plurality of drive and driven face teeth are configured to deflect upon receiving torque greater than the predetermined torque such that the plurality of drive teeth slip relative to the plurality of driven teeth for limiting torque transmission to the driven disc.

Example 12

The surgical instrument of any one or more of Examples 10 through 11, wherein one of the drive and driven discs includes a wave spring and the remaining one of the drive and driven discs includes a plurality of projections rotatably secured with the wave spring up to the predetermined torque, wherein the wave spring is configured to deflect upon receiving torque greater than the predetermined torque such that the wave spring slips relative to the plurality of projections for limiting torque transmission to the driven disc.

Example 13

The surgical instrument of any one or more of Examples 10 through 12, wherein the drive and driven discs are positioned within the knob.

Example 14

The surgical instrument of any one or more of Examples 10 through 13, wherein the drive and driven discs are positioned proximally from the knob and configured to be received within an instrument body with the ultrasonic transducer assembly.

Example 15

The surgical instrument of any one or more of Examples 10 through 14, further comprising: (a) an instrument body; (b) an ultrasonic transducer assembly configured to rotatably couple with the proximal end portion of the acoustic waveguide, wherein the ultrasonic transducer assembly is rotatably mounted along a longitudinal axis within the instrument body such that the ultrasonic transducer assembly is configured to selectively rotate about the longitudinal axis; and (c) a transducer lock operatively connected to the instrument body and having a lock member configured to be selectively moved between an unlocked position and a locked position, wherein the ultrasonic transducer assembly is configured to be selectively rotated about the longitudinal axis relative to the instrument body with the lock member in the unlocked position, and wherein the transducer lock is configured to seize the ultrasonic transducer assembly with the lock member in the locked position to thereby selectively inhibit rotation about the longitudinal axis relative to the housing for rotatably coupling with the acoustic waveguide.

Example 16

A surgical instrument, comprising: (a) an end effector; (b) a shaft assembly having an acoustic waveguide extending therethrough, wherein the end effector projects distally from the shaft assembly, and wherein the acoustic waveguide has a proximal end portion configured to rotatably couple with an ultrasonic transducer assembly; and (c) a torque wrench integrally connected with the shaft assembly, wherein the torque wrench includes an arrester selectively movable between a disengaged position and an engaged position, wherein the arrester in the disengaged position is configured to allow the ultrasonic transducer assembly to rotate, and wherein the arrester in the engaged position is configured to engage an engagement feature connected to the ultrasonic transducer assembly for inhibiting rotation of the ultrasonic transducer assembly up to the predetermined torque, wherein the arrester is further configured to deflect upon receipt of torque greater than the predetermined torque and disengage from the engagement feature for relative slip between the arrester and the engagement feature thereby limiting coupling of the acoustic waveguide to the ultrasonic transducer assembly to the predetermined torque.

Example 17

The surgical instrument of Example 16, further comprising: (a) an instrument body; and (b) an ultrasonic transducer assembly configured to rotatably couple with the proximal end portion of the acoustic waveguide and rotatably mounted along a longitudinal axis within the instrument body such that the ultrasonic transducer assembly is configured to selectively rotate about the longitudinal axis, wherein the engagement feature is connected to the ultrasonic transducer assembly such that inhibiting rotation of the engagement feature thereby inhibits rotation of the ultrasonic transducer assembly, and wherein the arrester is configured to deflect upon receipt of torque greater than the predetermined torque and disengage from the engagement feature such that the engagement feature is configured to rotatably slip relative to the arrester.

Example 18

A surgical instrument, comprising: (a) an end effector; (b) a shaft assembly having the end effector projecting distally therefrom, wherein the shaft assembly includes: (i) a shaft assembly body, (ii) a knob rotatably connected to the shaft assembly body, and (iii) an acoustic waveguide extending through the knob and having a proximal end portion configured to rotatably couple with an ultrasonic transducer assembly; and (c) a torque wrench integrally connected with the shaft assembly, the torque wrench including: (i) a drive feature rotatably secured relative to the knob such that rotating the knob simultaneously rotates the drive feature, and (ii) a driven feature rotatably secured relative to the acoustic waveguide such that rotating the driven feature simultaneously rotates the acoustic waveguide, wherein the drive feature is engaged with the driven feature to transmit torque from the knob to the acoustic waveguide up to a predetermined torque, and wherein the driven feature is configured to rotatably slip relative to the drive feature upon receiving torque greater than the predetermined torque for limiting coupling of the acoustic waveguide to the ultrasonic transducer assembly to the predetermined torque via the knob.

Example 19

The surgical instrument of Example 18, further comprising: (a) an instrument body; and (b) an ultrasonic transducer assembly configured to rotatably couple with the proximal end portion of the acoustic waveguide, wherein the ultrasonic transducer assembly is rotatably mounted along a longitudinal axis within the instrument body such that the ultrasonic transducer assembly is configured to selectively rotate about the longitudinal axis.

Example 20

The surgical instrument of Example 19, further comprising a transducer lock operatively connected to the instrument body and having a lock member configured to be selectively moved between an unlocked position and a locked position, wherein the ultrasonic transducer assembly is configured to be selectively rotated about the longitudinal axis relative to the instrument body with the lock member in the unlocked position, and wherein the transducer lock is configured to seize the ultrasonic transducer assembly with the lock member in the locked position to thereby selectively inhibit rotation about the longitudinal axis relative to the housing for rotatably coupling with the acoustic waveguide.

IV. MISCELLANEOUS

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:

(a) an end effector;

(b) a shaft assembly having the end effector projecting distally therefrom, wherein the shaft assembly includes an acoustic waveguide extending therethrough and a proximal end portion configured to rotatably couple with an ultrasonic transducer assembly; and (c) a torque wrench integrally connected with the shaft assembly, the torque wrench including a drive feature configured to engage with a driven feature to transmit torque from the shaft assembly to the acoustic waveguide up to a predetermined torque, wherein the drive feature is configured to slip relative to the driven feature upon receiving torque greater than the predetermined torque for limiting coupling of the acoustic waveguide to the ultrasonic transducer assembly to the predetermined torque, the drive feature including a drive disc positioned coaxially with the acoustic waveguide.

2. The surgical instrument of claim 1, wherein the drive feature is rotatably secured relative to at least a portion of the shaft assembly such that rotating the at least the portion of the shaft assembly simultaneously rotates the drive feature.

3. The surgical instrument of claim 1, wherein the torque wrench further includes a driven feature, wherein the driven feature is rotatably secured relative to the acoustic waveguide such that rotating the driven feature simultaneously rotates the acoustic waveguide.

4. The surgical instrument of claim 3, wherein the driven feature is configured to abut against the drive feature.

5. The surgical instrument of claim 1, wherein the torque wrench further includes a driven feature, wherein the driven feature includes a driven disc rotatably secured relative to the acoustic waveguide such that rotating the driven feature simultaneously rotates the acoustic waveguide.

6. The surgical instrument of claim 1, wherein the drive feature includes a drive disc having a wave spring.

7. The surgical instrument of claim 6, wherein the torque wrench further includes a driven feature, wherein the driven feature includes a driven disc having a plurality of projections configured to configured to releasably engage with the wave spring.

8. The surgical instrument of claim 1, further comprising an instrument body, wherein the shaft assembly is configured to removably connect to the instrument body.

9. The surgical instrument of claim 8, further comprising an ultrasonic transducer assembly positioned within the instrument body.

10. The surgical instrument of claim 9, further comprising an engagement feature connected to the ultrasonic transducer assembly, wherein the engagement feature is configured to be engaged by an arrester to selectively rotatably secure the ultrasonic transducer assembly relative to the shaft assembly.

11. The surgical instrument of claim 1, further comprising:

(a) a lock member configured to be selectively translated from an unlocked position to a locked position; and (b) an arrester operatively connected to the lock member and configured to selectively translate between a disengaged position and an engaged position as the lock member is respectively translated between the unlocked position and the locked position, wherein the arrester is configured to engage an engagement feature connected to the ultrasonic transducer assembly for inhibiting rotation of the ultrasonic transducer assembly thereto up to the predetermined torque.

12. The surgical instrument of claim 11, wherein the shaft assembly further includes a shaft assembly body having a switch channel, wherein the lock member includes a lock switch movably mounted in the switch channel, and wherein the lock switch is configured to be manipulated by a user between the locked and unlocked positions.

13. The surgical instrument of claim 1, wherein the shaft assembly further includes a knob rotatably connected to drive feature such that rotating the knob simultaneously rotates the drive feature.

14. The surgical instrument of claim 1, wherein the torque wrench is configured to provide a select one or both of an audible indicator and a tactile indicator when the waveguide is coupled with the ultrasonic transducer assembly at the predetermined torque.

15. A surgical instrument, comprising:

(a) an instrument body;

(b) an ultrasonic transducer assembly positioned at least partially within the instrument body and configured to rotate about an axis, wherein the ultrasonic transducer assembly is configured to connect to an acoustic waveguide of a shaft assembly;

(c) a lock member configured to be selectively translated from an unlocked position to a locked position; and (d) an engagement feature connected to the ultrasonic transducer assembly, wherein the engagement feature is configured to be engaged by an arrester operatively connected to the lock member to selectively inhibit rotation of the ultrasonic transducer assembly up to a predetermined torque about the axis for rotatably securing the ultrasonic transducer assembly relative to the instrument body according to whether the lock member is in the locked or unlocked position.

16. The surgical instrument of claim 15, further comprising a torque wrench operatively connected with the shaft assembly, the torque wrench including a drive feature configured to engage with a driven feature to transmit torque from the shaft assembly to the acoustic waveguide up to the predetermined torque, wherein the drive feature is configured to slip relative to the driven feature upon receiving torque greater than the predetermined torque for limiting coupling of the acoustic waveguide to the ultrasonic transducer assembly to the predetermined torque.

17. The surgical instrument of claim 15, wherein the engagement feature includes an engagement collar with a plurality of teeth projecting radially therefrom.

18. The surgical instrument of claim 17, wherein the arrester includes a catch cam configured to engage with the plurality of teeth of the engagement collar, and wherein the catch cam includes a cam surface which, upon application of a torque greater than the predetermined torque, will interface with at least one tooth of the plurality of teeth such that the catch cam is directed out of engagement with the plurality of teeth and rotatably releases the engagement collar.

19. A method of coupling an acoustic waveguide to an ultrasonic transducer assembly with a predetermined torque for a surgical instrument, the surgical instrument including an end effector; a shaft assembly having the end effector projecting distally therefrom, wherein the shaft assembly includes an acoustic waveguide extending therethrough and a proximal end portion configured to rotatably couple with an ultrasonic transducer assembly; and a torque wrench integrally connected with the shaft assembly, the torque wrench including a drive feature configured to engage with a driven feature to transmit torque from the shaft assembly to the acoustic waveguide up to a predetermined torque, wherein the drive feature is configured to slip relative to the driven feature upon receiving torque greater than the predetermined torque for limiting coupling of the acoustic waveguide to the ultrasonic transducer assembly to the predetermined torque, the drive feature including a drive disc, the method comprising:

(a) inhibiting rotation of the ultrasonic transducer assembly about an axis;

(b) rotating the acoustic waveguide into the ultrasonic transducer assembly threadably coupling the acoustic waveguide with the ultrasonic transducer assembly;

(c) tightening the acoustic waveguide into the ultrasonic transducer assembly up to the predetermined torque thereby coupling the acoustic waveguide with the ultrasonic transducer assembly; and (d) slipping the drive disc of the drive feature relative to the driven feature upon reaching the predetermined torque to inhibit overtightening the acoustic waveguide into the ultrasonic transducer assembly.

20. The surgical instrument of claim 5, wherein the drive disc includes a plurality of drive face teeth extending therefrom towards the driven disc, and wherein the driven disc includes a plurality of driven face teeth extending therefrom towards the drive disc to releasably engage with the plurality of drive face teeth.

* * * * *